United States Patent
May

(10) Patent No.: US 11,344,545 B2
(45) Date of Patent: *May 31, 2022

(54) USE OF LEVOCETIRIZINE AND MONTELUKAST IN THE TREATMENT OF AUTOIMMUNE DISORDERS

(71) Applicant: IRR, INC., Santa Barbara, CA (US)

(72) Inventor: Bruce Chandler May, Santa Barbara, CA (US)

(73) Assignee: IRR, INC., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/224,129

(22) Filed: Dec. 18, 2018

(65) Prior Publication Data

US 2019/0201392 A1    Jul. 4, 2019

Related U.S. Application Data

(63) Continuation of application No. 15/584,795, filed on May 2, 2017, now Pat. No. 10,201,537, which is a continuation of application No. 14/831,339, filed on Aug. 20, 2015, now Pat. No. 9,669,026, which is a continuation of application No. PCT/US2014/021784, filed on Mar. 7, 2014.

(60) Provisional application No. 61/780,420, filed on Mar. 13, 2013.

(51) Int. Cl.

| | |
|---|---|
| A61K 31/495 | (2006.01) |
| A61K 31/4985 | (2006.01) |
| A61K 31/135 | (2006.01) |
| A61K 38/19 | (2006.01) |
| A61K 31/136 | (2006.01) |
| A61K 31/454 | (2006.01) |
| A61K 31/47 | (2006.01) |
| A61K 31/519 | (2006.01) |
| A61K 31/573 | (2006.01) |
| A61K 31/496 | (2006.01) |

(52) U.S. Cl.
CPC .......... *A61K 31/495* (2013.01); *A61K 31/135* (2013.01); *A61K 31/136* (2013.01); *A61K 31/454* (2013.01); *A61K 31/47* (2013.01); *A61K 31/496* (2013.01); *A61K 31/4985* (2013.01); *A61K 31/519* (2013.01); *A61K 31/573* (2013.01); *A61K 38/193* (2013.01)

(58) Field of Classification Search
CPC .............................. A61K 31/495; A61K 31/47
See application file for complete search history.

(56) References Cited

U.S. PATENT DOCUMENTS

| | | |
|---|---|---|
| 4,801,612 A | 1/1989 | Wei et al. |
| 5,147,637 A | 9/1992 | Wright et al. |
| 5,211,958 A | 5/1993 | Akkerboom et al. |
| 5,540,225 A | 7/1996 | Schutt |
| 6,384,038 B1 | 5/2002 | Rubin |
| 6,790,849 B2 | 9/2004 | Rubin |
| 7,166,640 B2 | 1/2007 | Berg |
| 7,186,555 B1 | 3/2007 | Tracey et al. |
| 7,226,470 B2 | 6/2007 | Kemény et al. |
| 7,291,331 B1 | 11/2007 | Croft et al. |
| 7,589,076 B2 | 9/2009 | Rieger et al. |
| 9,044,479 B2 | 6/2015 | May |
| 9,522,148 B2 | 12/2016 | May |
| 9,669,025 B2 | 6/2017 | May |
| 9,669,026 B2 | 6/2017 | May |
| 9,925,183 B2 | 3/2018 | May |
| 9,937,166 B2 | 4/2018 | May |
| 10,195,193 B2 | 2/2019 | May |
| 10,201,537 B2 | 2/2019 | May |
| 10,206,919 B2 | 2/2019 | May |
| 10,537,568 B2 | 1/2020 | May |
| 10,792,281 B2 | 10/2020 | May |
| 2001/0025040 A1 | 9/2001 | Poppe et al. |
| 2001/0033872 A1 | 10/2001 | Corson et al. |
| 2001/0051624 A1 | 12/2001 | Jones |
| 2002/0006961 A1 | 1/2002 | Katz et al. |
| 2002/0052312 A1 | 5/2002 | Reiss et al. |
| 2004/0180868 A1 | 9/2004 | Mullally |
| 2005/0256131 A1 | 11/2005 | Coester |
| 2006/0263350 A1 | 11/2006 | Lane |
| 2007/0020352 A1 | 1/2007 | Tripp et al. |
| 2007/0025987 A1 | 2/2007 | Brunetta |
| 2007/0225285 A1 | 9/2007 | Hutchinson et al. |

(Continued)

FOREIGN PATENT DOCUMENTS

| | | |
|---|---|---|
| CA | 2 802 853 | 12/2011 |
| CN | 102 895 661 | 1/2013 |

(Continued)

OTHER PUBLICATIONS

Wilson, D.C., Effect of an Anti-histamine in Rheumatoid Arthritis, 1952, European PMC, pp. 38-39 (Year: 1952).*
Permin et al., Possible Role of Histamine in Rheumatoid Arthritis, 1981, Allergy, 36, pp. 435-436 (Year: 1981).*
Mathis et al., Role of Leukotriene B4 Receptors in Rheumatoid Arthritis, 2007, Autoimmun Rev., 7(1), pp. 12-17 (Year: 2007).*
Matteson, EL, Current Treatment Strategies for Rheumatoid Arthritis, 2000, Mayo Clin Proc., 75, pp. 69-74 (Year: 2000).*
Al-Ahmad, Mona, "Omalizumab Therapy in Three Patients with Chronic Autoimmune Urticaria", Annals of Saudi Medicine, vol. 30, No. 6, Nov.-Dec. 2010, pp. 478-481.

(Continued)

*Primary Examiner* — James D. Anderson
(74) *Attorney, Agent, or Firm* — Knobbe, Martens, Olson & Bear, LLP

(57) ABSTRACT

The embodiments described herein include methods and formulations for treating autoimmune disorders. The methods and formulations include, but are not limited to, methods and formulations for delivering effective concentrations of levocetirizine and montelukast to a patient in need. The methods and formulations can comprise conventional and/or modified-release elements, providing for drug delivery to the patient.

22 Claims, 4 Drawing Sheets

(56) References Cited

U.S. PATENT DOCUMENTS

| | | |
|---|---|---|
| 2007/0244128 A1 | 10/2007 | Hutchinson et al. |
| 2008/0260644 A1 | 10/2008 | Cohen |
| 2010/0305080 A1 | 12/2010 | O'Shea |
| 2012/0040892 A9 | 2/2012 | Zimmer et al. |
| 2012/0053563 A1 | 3/2012 | Du |
| 2012/0071509 A1 | 3/2012 | Gore et al. |
| 2012/0190691 A1 | 7/2012 | Bouyssou et al. |
| 2012/0263764 A1 | 10/2012 | Watson |
| 2013/0011395 A1 | 1/2013 | Spies et al. |
| 2013/0029949 A1 | 1/2013 | Hoffmann et al. |
| 2013/0030000 A1 | 1/2013 | Chobanian et al. |
| 2013/0030009 A1 | 1/2013 | Harish et al. |
| 2013/0085124 A1 | 4/2013 | May |
| 2015/0231133 A1 | 8/2015 | May |
| 2015/0352101 A1 | 12/2015 | May |
| 2015/0352102 A1 | 12/2015 | May |
| 2015/0352103 A1 | 12/2015 | May |
| 2015/0352104 A1 | 12/2015 | May |
| 2016/0175301 A1 | 6/2016 | May |
| 2017/0056395 A1 | 3/2017 | May |
| 2017/0173001 A1 | 6/2017 | May |
| 2017/0231980 A1 | 8/2017 | May |
| 2017/0368059 A1 | 12/2017 | May |
| 2018/0169091 A1 | 6/2018 | May |
| 2018/0185357 A1 | 7/2018 | May |
| 2019/0091218 A1 | 3/2019 | May |
| 2019/0201393 A1 | 7/2019 | May |
| 2019/0298714 A1 | 10/2019 | May |
| 2020/0101067 A1 | 4/2020 | May |
| 2020/0323843 A1 | 10/2020 | May |
| 2021/0177835 A1 | 6/2021 | May |

FOREIGN PATENT DOCUMENTS

| | | |
|---|---|---|
| CN | 103 505 731 | 1/2014 |
| EP | 1 769 797 | 4/2007 |
| EP | 2 520 292 | 7/2012 |
| EP | 2 799 071 | 11/2014 |
| JP | 2001-511134 | 8/2001 |
| JP | 2001-526232 | 12/2001 |
| JP | 2002-511425 | 4/2002 |
| JP | 2004-536097 | 12/2004 |
| JP | 2009-520711 | 5/2009 |
| JP | 2009-525952 | 7/2009 |
| JP | 2011-500847 | 1/2011 |
| JP | 2012-519207 | 8/2012 |
| JP | 2013-528654 | 7/2013 |
| KR | 10-2001-0033485 | 4/2001 |
| RU | 2442789 | 6/2010 |
| WO | WO 95/009652 | 4/1995 |
| WO | WO 99/032125 | 7/1999 |
| WO | WO 99/052553 | 10/1999 |
| WO | WO 03/002098 | 1/2003 |
| WO | WO 03/002109 | 1/2003 |
| WO | WO 03/101434 | 12/2003 |
| WO | WO 2006/010283 | 2/2006 |
| WO | WO 2008/100539 | 8/2008 |
| WO | WO 2008/106429 | 9/2008 |
| WO | WO 2009/022327 | 2/2009 |
| WO | WO 2009/055729 | 4/2009 |
| WO | WO 2010/107404 | 9/2010 |
| WO | WO 2011/003074 | 1/2011 |
| WO | WO 2011/041462 | 4/2011 |
| WO | WO 2011/094209 | 8/2011 |
| WO | WO 2011/159821 | 12/2011 |
| WO | WO 2012/064301 | 5/2012 |
| WO | WO 2012/064305 | 5/2012 |
| WO | WO 2012/092594 | 7/2012 |
| WO | WO 2013/012199 | 1/2013 |
| WO | WO 2013/013490 | 1/2013 |
| WO | WO 2013/148366 | 10/2013 |
| WO | WO 2014/090990 | 6/2014 |
| WO | WO 2014/164281 | 10/2014 |
| WO | WO 2014/164282 | 10/2014 |
| WO | WO 2014/164285 | 10/2014 |
| WO | WO 2014/164299 | 10/2014 |
| WO | WO 2016/044095 | 3/2016 |
| WO | WO 2017/210417 | 12/2017 |

OTHER PUBLICATIONS

Athanasiadis et al., "Urticarial Vasculitis With a Positive Autologous Serum Skin Test: Diagnosis and Successful Therapy", Allergy, 2006, vol. 61, pp. 1484-1485.

Bisgaard Hans, "A Randomized Trial of Montelukast in Respiratory Syncytial Virus Postbronchiolitis", American Journal of Respiratory and Critical Care Medicine, 2003, vol. 167, No. 3, pp. 379-383.

Borish MD, Larry, "Allergic Rhinitis: Systemic Inflammation and Implications for Management", The Journal of Allergy and Clinical Immunology, Dec. 1, 2003, pp. 1021-1031.

Ciebieada, MD et al., "Montelukast with Desloratadine or Levocetirizine for the Treatment of Persistent Allergic Rhinitis", Annals of Allergy, Asthma & Immunology, Nov. 2006, vol. 97, pp. 664-671.

Clinical Surgery, 1999, Oct. 3, vol. 54, No. 11, Special Issue, pp. 13-15.

Dávila et al., "Effect of H1 Antihistamines Upon the Cardiovascular System", Journal of Investigational Allergology and Clinical Immunology, 2006, vol. 16, No. 1, pp. 13-23.

Eccles, Ron, "Understanding the Symptoms of the Common Cold and Influenza", The Lancet Infectious Diseases, R(1) Nov. 2005, vol. 5, No. 11, pp. 718-725.

El-Shanawany et al., "Clinical Immunology Review Series: An Approach to the Patient with Anaphylaxis", British Society for Immunology, Clinical and Experimental Immunology, 2008, vol. 153, pp. 1-9.

Fedson, David, "A Practical Treatment for Patients with Ebola Virus Disease", Journal of Infectious Diseases, Aug. 25, 2014, pp. 5.

Fedson, David, "Treating Influenza with Statins and Other Immunomodulatory Agents", Antiviral Research, Sep. 2013, vol. 99, No. 3, pp. 417-435.

Glantschnig et al., "Mass Fraction Profiling Based on X-Ray Tomography and its Application to Characterizing Porous Silica Boules", Applied Optics, Mar. 15, 1987, vol. 26, No. 6, pp. 983-989.

Heneka et al., "Innate Immune Activation in Neurodegenerative Disease", Nature Reviews, Immunology, Jul. 2014, vol. 14, pp. 463-477.

Hong et al., "Urticaria and Angioedema", Cleveland Clinic—Center for Continuing Education, Aug. 2010, pp. 11.

Ingelsson et al., "Nationwide Cohort Study of the Leukotriene Receptor Antagonist Montelukast and Incident or Recurrent Cardiovascular Disease", Journal of Allergy and Clinical Immunology, Mar. 2012, vol. 129, No. 3, pp. 702-707.e2.

Jang et al., "Levoceterizine Inhibits Rhinovirus-Induced ICAM-1 and Cytokine Expression and Viral Replication in Airway Epithelial Cells", Antiviral Research, Mar. 2009, vol. 81, No. 3, pp. 226-233.

Jensen et al., "Sensing of RNA Viruses: a Review of Innate Immune Receptors Involved in Recognizing RNA Virus Invasion", Journal of Virology, Mar. 2012, vol. 86, No. 6, pp. 2900-2910.

Jianxin et al., "Therapeutic Effectiveness Analysis of Montelukast in Therapy of Anaphylactic Purpura", Journal of Clinical and Experimental Medicine, May 2010, vol. 9, No. 10, pp. 782-783.

Khoury, MD et al., "Effect of Montelukast on Bacterial Sinusitis in Allergic Mice", Annals of Allergy, Asthma & Immunology, Sep. 2006, vol. 97, No. 3, pp. 329-335.

Kozel et al., "Chronic Urticaria: Aetiology, Management and Current and Future Treatment Options," Drugs, 2004, vol. 64, No. 22, pp. 2515-2536.

Kronenberg et al., "Symptomatic Treatment of Uncomplicated Lower Urinary Tract Infections in the Ambulatory Setting: Randomised, Double Blind Trial", BMJ, 2017, vol. 359, No. J4787, pp. 10.

Kuna et al., "Two Phase II Randomized Trials on the CR Th2 Antagonist AZD1981 in Adults with Asthma", Drug Design, Development and Therapy, 2016, vol. 10, pp. 2759-2770.

Kurowski et al., "Montelukast Plus Cetirizine in the Prophylactic Treatment of Seasonal Allergic Rhinitis: Influence of Clinical Symptoms and Nasal Allergic Inflammation", Allergy, 2004, vol. 59, pp. 280-288.

(56) References Cited

OTHER PUBLICATIONS

Lishchuk-Yakymovych et al., "Positive Correlation Between Serum IL-5 and TNF-alpha Levels and Churg-Strauss Syndrome Activity in Patients Successfully Treated with Motelukast", Journal of Allergy and Clinical Immunology, Entry 295, Feb. 2012, p. 1.
Luthra et al., "Mutual Antagonism between the Ebola Virus VP35 Protein and the RIG-1 Activator PACT Determines Infection Outcome", Cell Host Microbe, Jul. 17, 2013, vol. 14, No. 1, pp. 1-23.
Mansi et al., "ANCA-Associated Small-Vessel Vasculitis", American Family Physician, Apr. 15, 2002, vol. 65, No. 8, pp. 1615-1620.
Mathiesen et al., "On the Mechanism of Interaction of Potent Surmountable and Insurmountable Antagonists with the Prostaglandin D2 Receptor CRTH2", Molecular Pharmacology, 2006, vol. 69, No. 4, pp. 1441-1453.
May, B. Chandler, "A Proposed Model for the Treatment of Acute Inflammation", Mazatlán, Mexico, LXIV Conference of the Mexican College of Clinical Immunology and Allergy, May 29, 2010, pp. 3.
May, B. Chandler, "Contemporary Treatment of Influenza", Santa Barbara, CA, 25th Annual Infectious Disease Conference, Dec. 18, 2009, pp. 36.
McElroy et al., Ebola Hemorrhagic Fever: Novel Biomarker Correlates of Clinical Outcome, Journal of Infectious Disease, Aug. 15, 2014, vol. 210, No. 4, pp. 558-566.
McKinney et al., "The Immunopatholgy of ANCA-Associated Vasculitis", Semin Immunopathol, 2014, vol. 36, pp. 461-478.
Min et al., "Levocetirizine Inhibits Rhinovirus-Induced Bacterial Adhesion to Nasal Epithelial Cells Through Down-Regulation of Cell Adhesion Molecules", Annals of Allergy, Asthma and Immunology, 2012, vol. 108, pp. 44-48.
Modrykamien, MD et al., "The Acute Respiratory Distress Syndrome", Proceedings (Baylor University Medical Center) 2015, vol. 28, No. 2, pp. 163-171.
Moiz et al., "Formulation and Evaluation of Bilayered Tablets of Montelukast and Levocetrizine Dihydrocholoride Using Natural and Synthetic Polymers", International Journal of Drug Delivery 3, Jan. 2011, pp. 597-618.
Muller, Barbara A., "Urticaria and Angioedema: A Practical Approach", American Family Physician, 2004, vol. 69, No. 5, pp. 1123-1128.
Namazi, M.R. "Cetirizine and Allopurinol as Novel Weapons Against Cellular Autoimmune Disorders", International Immunopharmacology, 2004, vol. 4, pp. 349-353.
Nederkoorn et al., "Preventive Antibiotics in Stroke Study: Rationale and Protocol for a Randomised Trial", International Journal of Stroke, Apr. 2011, vol. 6, pp. 159-163.
Nonaka et al., "Prolonged Activation of NF-κB Following Traumatic Brain Injury in Rats", Journal of Neurotrauma, Nov. 1999, vol. 16, No. 11, pp. 1023-1034.
Parker, MD et al., "A 48 Year Old Man with Recurrent Sinusitis, 1 Year Later", JAMA, Clinical Crossroads Update, Jan. 24/31, 2001, vol. 285, No. 4, p. 462.
Peroni et al., "Combined Cetirizine-Montelukast Preventative Treatment for Food-Dependent Exercise-Induced Anaphylaxis", Annals of Allery, Asthma, & Immunology, Mar. 2010, vol. 104, pp. 272-273.
Popov et al., "A Comparison of Levocetirizine and Desloratadine in the Histamine-Induced Wheal and Flare Response in Human Skin in Vivo", Inflammatory Research, Jun. 2006, vol. 55, No. 6, pp. 241-244.
"Prostaglandin DP2 receptor", Wikipedia, <https://en.wikipedia.org/wiki/Prostaglandin_DP2_receptor>, Aug. 25, 2017, pp. 9.
Pushparaj et al., "The Cytokine Interleukin-33 Mediates Anaphylactic Shock", with Retraction and Correction, Proceeding of the National Academy of Sciences of the United States of America (PNAS), Jun. 16, 2009, vol. 106, No. 24, pp. 9773-9778.
Quercia et al., "Adalimumab Desensitization after Anaphylactic Reaction", Allergy, 2010, vol. 65, No. 92, pp. 242-243.
Radlińska et al., "Montelukast—Recent Advances in Determining the Role of Leukotriene Inhibitor in Allergic Diseases", International Review of Allergology and Clinical Immunology, Jan. 2011, vol. 17:1-2, pp. 35-39.
Roumestan et al., "Histamine H1-receptor antagonists inhibit nuclear factor-kappaB and activator protein-1 activities via H1-receptor-dependent and -independent mechanisms", Clinical and Experimental Allergy, Jun. 2008, vol. 38, No. 6, pp. 947-956.
Schad et al., "Effect of Montelukast on Pro-inflammatory Cytokine Production During Naturally Acquired Viral Upper Respiratory Infections (vURIs) in Adults", Journal of Allergy and Clinical Immunology, Elsevier, Amsterdam, NL, Feb. 2008, vol. 121, No. 2, p. S74.
Singh-Franco et al., "Levocetirizine for the Treatment of Allergic Rhinitis and Chronic Idiopathic Urticaria in Adults and Children", Clinical Therapeutics, vol. 31, No. 8, Aug. 2009, pp. 1664-1687.
Spiropoulou et al., "RIG-I Activation Inhibits ebolavirus Replication", Virology, 2009, 392, pp. 11-15.
Taber's® Cyclopedic Medical Dictionary, "Trauma", 18th Edition, 1997, pp. 1988-1989.
Tang, Angela, "A Practical Guide to Anaphylaxis", American Family Physician, Oct. 1, 2013, vol. 68, No. 7, pp. 1325-1333.
Tillement et al., "Compared Pharmacological Characteristics in Humans of Racemic Cetirizine and Levocetirizine, Two Histamine H1-Receptor Antagonists", Biochemical Pharmacology, 2003, pp. 1123-1126.
Tillie-Leblond et al., "Relation Between Inflammation and Symptoms in Asthma", Allergy, vol. 64, No. 3, Mar. 1, 2009, pp. 354-367.
Wong et al., "Characterization of Host Immune Responses in Ebola Virus Infections", Expert Review of Clinical Immunology, 2014, vol. 10, No. 6, pp. 781-790.
Wu et al., "Add-On Therapy with Montelukast in the Treatment of Henoch-Schönlein Purpura", Pediatrics International, 2014, vol. 56, pp. 315-322.
Yu et al., "Montelukast, a Cysteinyl Leukotriene Receptor-1 Antagonist, Dose- and Time-Dependently Protects Against Focal Cerebral Ischemia in Mice", Pharmacology, Jan. 2005, vol. 73, No. 1, pp. 31-40.
Zana, Larry, "Qrono—Reformulating known, approved drugs", as printed Jun. 23, 2014, pp. 12.
Zhang et al., "Contrastive Observation of Loratadine and Cetirizine in Therapy of Anaphylactic Purpura", Chinese Remedies & Clinics, May 2008, pp. 65-66.
Bernier et al., "Consensus Guidelines for the Management of Radiation Dermatitis and Coexisting Acne-Like Rash in Patients Receiving Radiotherapy Plus EGFR Inhibitors for the Treatment of Squamous Cell Carcinoma of the Head and Neck", Annals of Oncology, vol. 19, 2008, pp. 142-149.
Deb et al., "Pathophysiologic Mechanisms of Acute Ischemic Stroke: An Overview with Emphasis on Therapeutic Significance Beyond Thrombolysis", Pathophysiology, 2010, vol. 17, pp. 197-218.
Elting et al., "Comparison of Serum S-100 Protein Levels Following Stroke and Traumatic Brain Injury", Journal of the Neurological Sciences, 2000, vol. 181, pp. 104-110.
International Preliminary Report on Patentability received in PCT Application No. PCT/US2014/021784, dated Sep. 24, 2015 in 8 pages.
International Search Report and Written Opinion received in PCT Application No. PCT/US2014/021784, dated Jun. 23, 2014 in 9 pages.
Medzhitov, Ruslan, "Origin and Physiological Roles of Inflammation," Nature, vol. 454, Jul. 24, 2008, pp. 428-435.
Murdoch et al., "Chronic Inflammation and Asthma", Mutation Research: Fundamental and Molecular Mechanisms of Mutagenesis, 2010, vol. 690, pp. 24-39.
Pellicane, MD, et al., "Calorie and Protein Intake in Acute Rehabilitation Inpatients with Traumatic Spinal Cord Injury Versus Other Diagnoses", Topics in Spinal Cord Injury Rehabilitation, 2013, vol. 19, No. 3, pp. 229-235.
Rosen et al., "New Approaches to Radiation Protection," Frontiers in Oncology, Jan. 20, 2015, vol. 4, No. 381, pp. 1-15.

(56) References Cited

OTHER PUBLICATIONS

Vasculitis Foundation, http://vasculitisfoundation.org/education/forms/urticarial-vasculitis/, 2017.
Zappalà et al., "Traumatic brain injury and the frontal lobes: What can we gain with diffusion tensor imaging?" Cortex, 2011, pp. 1-10.
Lai et al., "Montelukast Targeting the Cysteinyl Leukotriene Receptor 1 Ameliorates Aβ1-42-Induced Memory Impairment and Neuroinflammatory and Apoptotic Responses in Mice", Neuropharmacology, Apr. 2014, vol. 79, pp. 707-714.
Garau et al., "Radiobiology of the Acute Radiation Syndrome", Reports of Practical Oncology and Radiotherapy, 2011, vol. 16, pp. 123-130.
"Laboratory Tests Used in the Diagnosis and Monitoring of Rheumatoid Arthritis", National Rheumatoid Arthritis Society (NRAS), reviewed Nov. 4, 2019 and printed Sep. 2, 2020 in 4 pages. https://www.nras.org.uk/laboratory-tests-used-in-the-diagnosis-and-monitoring-of-rheumatoid-arthritis.
Williams et al., "Animal Models and Medical Countermeasures Development for Radiation-Induced Lung Damage: Report from an NIAID Workshop", Radiation Research, 2012, vol. 177, No. 5, pp. 25-39.
Commission on Accreditation of Rehabilitation Facilities Medical Rehabilitation Standards Manual ("CARF"), Jul. 1, 2020-Jun. 30, 2021, p. 397.
Fookes, Carmen, "Methylprednisolone vs Prednisone—What's the Difference Between Them?", Drugs.com, https://www.drugs.com/medical-answers/difference-between-methylprednisolone-prednisone-3509126/, as updated Aug. 17, 2021, pp. 3.
Gil et al. "COVID-19: Drug Targets and Potential Treatments," Journal of Medical Chemistry, 2020, 63, pp. 12359-12386.
Johnson, MD, et al., "Levocetirizine and Rupatadine in Chronic Idiopathic Urticaria", International Journal of Dermatology, 2015, vol. 54, pp. 1199-1204.
Marshall, III, M.D., William F., "COVID-19 (coronavirus) drugs: Are there any that work?" Mayo Clinic, Mayo Foundation for Medical Education and Research (MFMER). Jun. 2, 2021, 4 pages.
Matsen III M.D., "Rheumatoid Arthritis", https://orthop.washington.edu/patient-care/articles/arthritis/rheumatoid-arthritis.html, printed Aug. 30, 2021 in 11 pages.
Medrol®, Methylprednisolone tablets, USP, Pfizer, Revised Jul. 2018, pp. 13.
Menon, MD, PhD et al., "Position Statement: Definition of Traumatic Brain Injury", Archives of Physical Medicine and Rehabilitation, vol. 91, Nov. 2010, pp. 1637-1640.
Mostafa et al., "Comparative Study Evaluating Antihistamine Versus Leukotriene Receptor Antagonist as Adjuvant Therapy for Rheumatoid Arthritis", European Journal of Clinical Pharmacology, Jul. 4, 2021, pp. 10.
National Institute of Health (NIH), "Therapeutic Management of Hospitalized Adults with COVID-19" COVID-19 Treatment Guidelines, Jul. 8, 2021, 10 pages.

\* cited by examiner

FIG. 2A

| | 13Apr12 12:45 | 06Apr12 13:30 | 03Apr12 14:30 | 30Mar12 13:15 | 28Mar12 13:49 | 26Mar12 13:28 | 26Mar12 13:18 | 24Mar12 15:50 | 23Mar12 12:00 | 22Mar12 14:58 | 20Mar13 16:00 | 19Mar12 17:08 | 18Mar12 20:51 | 16Mar12 16:20 | 09Mar12 13:20 | 07Mar12 14:30 |
|---|---|---|---|---|---|---|---|---|---|---|---|---|---|---|---|---|
| EKG | | | | | | | | | | | | | | | | |
| ⊟ EKG | | | | | | | | | | | | | | | | |
|   EKG Results: | | | | | | | | | | | | | | | | |
|   EKG Routine Component | | | | | | | | | | | | | | | | |
| Hematology | | | | | | | | | | | | | | | | |
| ⊟ Blood Count | | | | | | | | | | | | | | | | |
|   WBC Count | 4.4 | 5.3 | *⇨ 3.8 | | 6.6 NOTE:.. | | 8.4 | 5.2 | 6.7 | 5.8 | 4.9 | | 4.9 | | ⇨ 3.4 | ⇨ 3.0 |
|   Hemoglobin | ⇨ 9.5 | ⇨ 9.9 | *⇨ 9.8 | | ⇨ 9.3 NOTE:.. | | ⇨ 9.0 | ⇨ 8.7 | ⇨ 8.3 | ⇨ 8.3 | ⇨ 9.6 | | ⇨ 9.2 | | ⇨ 8.1 | ⇨ 7.6 |
|   Hematocrit | ⇨ 29.7 | ⇨ 31.5 | ⇨ 29.7 | | ⇨ 28.1 NOTE:.. | | ⇨ 28.0 | ⇨ 25.9 | ⇨ 25.0 | ⇨ 25.3 | ⇨ 29.1 | | ⇨ 27.9 | | ⇨ 24.9 | ⇨ 24.2 |
|   Platelet Count | 157 | ⇨ 133 | 166 | | 186 NOTE:.. | | 183 | 114 | *⇨ 109 | *⇨ 72 | *⇨ 53 | | *⇨ 68 | | *⇨ 93 | ⇨ 91 |

FIG. 2B

| | 07Jun12 11:07 | 04Jun12 11:42 | 02Jun12 07:00 | 01Jun12 15:00 | 29May12 10:31 | 25May12 15:49 | 21May12 11:58 | 18May12 14:00 | 14May12 14:25 | 11May12 15:40 | 07May12 14:02 | 04May12 15:00 | 30Apr12 11:07 | 27Apr12 15:50 | 23Apr12 13:55 | 20Apr12 12:40 | 17Apr12 10:18 |
|---|---|---|---|---|---|---|---|---|---|---|---|---|---|---|---|---|---|
| EKG | | | | | | | | | | | | | | | | | |
| ⊟ EKG | | | | | | | | | | | | | | | | | |
|   EKG Results: | | | | | | | | | | | | | | | | | |
|   EKG Routine Component | | | | | | | | | | | | | | | | | |
| Hematology | | | | | | | | | | | | | | | | | |
| ⊟ Blood Count | | | | | | | | | | | | | | | | | |
|   WBC Count | | | | 5.3 | 8.4 | | | 3.7 | | ⇨ 3.4 | | 4.9 | 7.0 | 5.5 | | 6.9 |
|   Hemoglobin | | | | 11.4 | 11.7 | | | 11.3 | | ⇨ 10.9 | | ⇨ 10.6 | ⇨ 10.9 | ⇨ 10.8 | | ⇨ 10.5 |
|   Hematocrit | | | | 33.6 | 35.2 | | | 34.1 | | ⇨ 32.9 | | ⇨ 32.5 | 33.2 | 33.5 | | ⇨ 31.2 |
|   Platelet Count | | | | 188 | 157 | | | ⇨ 129 | | 167 | | ⇨ 139 | ⇨ 121 | ⇨ 114 | | ⇨ 128 |

| | 05Sep12 16:30 | 31Aug12 12:55 | 22Aug12 15:15 | 24Aug12 10:08 | 20Aug12 16:30 | 16Aug12 11:05 | 13Aug12 11:01 | 11Aug12 13:22 | 06Aug12 12:06 | 03Aug12 14:40 | 30Jul12 12:14 | 26Jul12 12:55 | 26Jul12 12:54 | 23Jul12 14:03 | 20Jul12 13:00 | 16Jul12 13:55 | 13Jul12 15:00 | 09Jul12 12:33 |
|---|---|---|---|---|---|---|---|---|---|---|---|---|---|---|---|---|---|---|
| EKG | | | | | | | | | | | | | | | | | | |
| ⊟EKG | | | | | | | | | | | | | | | | | | |
|   EKG Results: | | | | | | | | | | | | | | | | | | |
|   EKG Routine Component | | | | | | | | | | | | | | | | | | |
| Hematology | | | | | | | | | | | | | | | | | | |
| ⊟Blood Count | | | | | | | | | | | | | | | | | | |
|   WBC Count | 4.8 | | ⇨ 3.9 | | 5.2 | 5.0 | | 4.7 | 6.9 | | 4.1 | | | | 4.0 | | 5.0 | |
|   Hemoglobin | 11.5 | | 11.2 | | 11.1 | 11.4 | | 12.2 | 11.5 | | 11.4 | | | | 11.2 | | 11.1 | |
|   Hematocrit | 34.7 | | 35.1 | | 33.7 | 34.1 | | 35.4 | 36.1 | | 35.4 | | | | 34.1 | | 33.7 | |
|   Platelet Count | ⇨ 113 | | ⇨ 122 | | ⇨ 117 | ⇨ 112 | | ⇨ 113 | ⇨ 123 | | ⇨ 118 | | | | ⇨ 135 | | ⇨ 141 | |

*FIG. 2C*

USE OF LEVOCETIRIZINE AND MONTELUKAST IN THE TREATMENT OF AUTOIMMUNE DISORDERS

CROSS-REFERENCE TO RELATED APPLICATIONS

This application is a continuation of U.S. patent application Ser. No. 15/584,795, filed May 2, 2017, which is a continuation of U.S. patent application Ser. No. 14/831,339, filed Aug. 20, 2015, which is a continuation of International Application No. PCT/US2014/021784, filed Mar. 7, 2014, which claims the benefit of priority to U.S. Provisional Patent Application No. 61/780,420, filed Mar. 13, 2013. The foregoing applications are fully incorporated herein by reference in their entireties for all purposes.

BACKGROUND

Autoimmunity is described as an immune response directed against an antigen within the body of the host. This definition is independent of whether the response is innate or acquired, and if acquired whether it is induced by a foreign or autochthonous antigen. In other words, if acquired, the response is induced by a foreign antigen or antigen found in the part of the body or locality in which it originates, such as that produced by a cancer. Autoimmunity usually involves both T-cell and B-cell responses in a three dimensional complex immunologic array. The primary requirement is an immune response directed to a self-antigen.

In dealing with human disease it is often difficult to establish causality. As such the diagnosis of an autoimmune disease may be established by direct evidence, indirect evidence or circumstantial evidence. Direct evidence usually involves the transfer of an antibody from a patient to a healthy recipient. Indirect evidence can be found in such disease states as: (a) the reproduction of disease in animals via immunization with a select antigen, (b) naturally occurring disease in animals resembling the human counterpart, and (c) disease created by manipulating the immune system. Circumstantial evidence, the lowest level of proof, is suggested by confirming the presence of autoantibodies. Another type of circumstantial evidence is identified from the finding that autoimmune diseases have a tendency to cluster, likely from defined or yet to be defined genetic susceptibility traits. From a pathological perspective, with few exceptions, all autoimmune diseases require the presence of self-reactive CD4 T lymphocytes.

A separate category of autoimmune diseases, the autoinflammatory diseases, exists in which there is no evidence of adaptive immunity in the form of self-reactive T cells. This latter group consists of a core of six disorders known as hereditary recurrent fever syndromes.

Clinically, physicians tend to categorize autoimmune diseases as systemic (such as in the case of systemic lupus erythematosis) or organ-specific (such as type I diabetes mellitus). Therapy has generally been directed to the specific disease and associated presentation. Four therapeutic approaches are usually employed, but the complex causes of the two categories of autoimmune disorders offer considerable challenges to the development of new therapies. Moreover, many of the current modalities—such as the immunomodulators, immuonosuppressants, steroids, and intravenous gamma globulin, to name a few—precipitate side effects that are worse than the underlying disease.

SUMMARY

Methods of treating autoimmune disorders in a patient in need thereof are disclosed. The method comprises administering to the patient an effective amount of a combination of levocetirizine and montelukast.

In a variation, a method of treating a symptom of an autoimmune disorder in a patient in need thereof is disclosed. The method comprises administering to the patient an effective amount of a combination of levocetirizine and montelukast.

In some embodiments, the autoimmune disorder is idiopathic thrombocytopenia purpura. In some embodiments, the autoimmune disorder is autoimmune neutropenia.

The combination of levocetirizine and montelukast may be administered at the onset of symptoms for any of the disclosed methods.

The combination of levocetirizine and montelukast may be administered in a sequential manner for any of the disclosed methods.

The combination of levocetirizine and montelukast may be administered in a substantially simultaneous manner for any of the disclosed methods.

In some embodiments of the disclosed methods, an additional active agent may be administered. The additional active agent may be a steroid.

In some embodiments, a glucocorticoid may be administered. The glucocorticoid may be prednisone. In some embodiments, the glucocorticoid may be methylprednisolone.

In some embodiments, the additional active agent can be an immunosuppressant. The immunosuppressant may be methotrexate.

In some embodiments, the additional active agent can be a supplement. The supplement may be ferrous gluconate. The supplement may also be vitamin C.

In some embodiments, an antibacterial may be administered. The antibacterial may be dapsone.

In some embodiments, the additional active agent is a protein. The protein may be filgrastim (Neupogen®).

In some embodiments, an immunomodulator may be administered. The immunomodulator may be lenalidomide (Revlimid®).

In some embodiments of the disclosed methods, the combination may be administered to the patient by one or more of the routes consisting of enteral, intravenous, intraperitoneal, inhalation, intramuscular, subcutaneous and oral.

In some embodiment, the levocetirizine and montelukast are administered by the same route.

One embodiment is directed to methods, formulations and kits for treating autoimmune disorders. The methods and formulations include, but are not limited to, methods and formulations for delivering effective concentrations of levocetirizine and montelukast to a patient in need. The methods and formulations can comprise conventional and/or modified-release elements, providing for drug delivery to the patient.

In some embodiments, the methods of treatment, formulations and kits may include e.g., a bilayer tablet, comprising levocetirizine and montelukast in separate layers, for daily administration. Alternatively, each medication may be administered separately (one tablet of levocetirizine and one tablet of montelukast per day in the evening). In some embodiments, a combination of levocetirizine and montelukast, either as a single formulation or as separate formulations, may be administered for 1, 2, 3, 4, 5, 6, 7, 8, 9, 10, 11, 12, 13, 14, 15 days or more for the treatment of autoimmune diseases. In several embodiments, the autoimmune disease may be idiopathic thrombocytopenia purpura or autoimmune neutropenia. The bilayer tablets or the separate tablets may be packaged in a blister pack supplied for a 7 to 10 day course of therapy, with instructions including indications, administration instructions and precautions. In some embodiments, a combination of levocetirizine and montelukast, either as a single formulation, such as a bilayer tablet, or as separate formulations, may be administered for approximately 1, 2, 3, 4, 5, 6, 7, 8, 9, 10, 11, 12 months or more for the treatment of chronic inflammation. In some embodiments, a combination of levocetirizine and montelukast, either as a single formulation, such as a bilayer tablet, or as separate formulations, may be administered for approximately 1 year, 2 years, 3 years, or more for the treatment of chronic inflammation. The bilayer tablets or the separate tablets may be packaged in a blister pack supplied for a 30 day course of therapy, with instructions including indications, administration instructions and precautions.

BRIEF DESCRIPTION OF THE DRAWINGS

FIG. 2A-2C shows platelet counts of a patient as described in Example 1.

DETAILED DESCRIPTION

Figure 1:
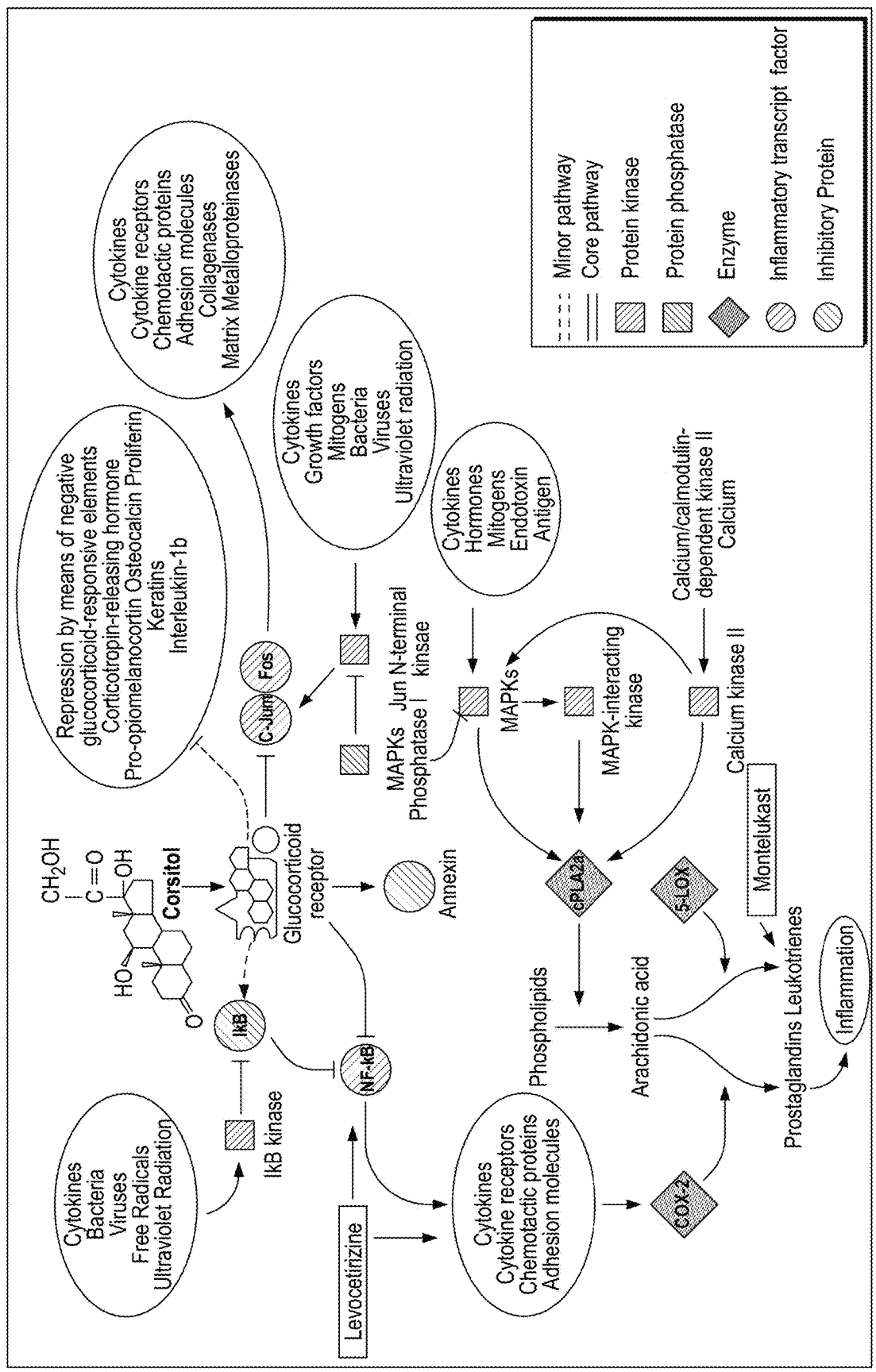
FIG. 1 shows a diagram of the proposed anti-inflammatory mechanism of action of levocetirizine and montelukast utilizing a steroid model pathway.

The present embodiments relate to the combination of levocetirizine and montelukast as a medicament for the treatment of acute, subacute and chronic inflammation. Several embodiments relate to the combination of levocetirizine and montelukast for the treatment of non-IgE-mediated, IgE-mediated, and/or combined non-IgE-mediated and IgE-mediated inflammation. Traditional allergic rhinitis is an IgE mediated disease; up to 70-80% of patients with asthma also have allergic rhinitis (atopic asthma). Administration of levocetirizine and montelukast in combination exhibits synergistic effects and unexpectedly superior results in the treatment of influenza, common cold, allergic rhinitis and acute, subacute, and chronic inflammation. Moreover, combinations of levocetirizine and montelukast can be used safely in conjunction with many existing treatment protocols.

Levocetirizine is an antihistamine and montelukast is a leukotriene receptor antagonist. As described herein, synergy between levocetirizine and montelukast shortens the course of the disease processes, thereby decreasing morbidity and mortality. This combined therapy also can improve quality of life from the amelioration of symptoms/side effects/disease process itself, and can decrease health-care costs. This synergistic effect can be observed in the use of a combination of levocetirizine and montelukast to treat non-IgE-mediated inflammation and combined non-IgE-mediated and IgE-mediated inflammation. Not wishing to be bound by a particular theory, the non-IgE-mediated response may be related, at least in part, to the fact that both levocetirizine and montelukast affect eosinophil migration, the leukocyte that is considered a hallmark of inflammation.

Levocetirizine, a potent H1-antihistamine, acts primarily by down-regulating the H1 receptor on the surface of mast cells and basophils to block the IgE-mediated release of histamine which cause the cardinal symptoms of allergic rhinitis: sneezing, rhinorrhea, nasal congestion, itchy palate and itchy red and watery eyes. Levocetirizine offers a short time to peak plasma level, 0.9 hr., a short time to steady state level, 40 hours, a low volume of distribution, 0.4 L/kg, and an enhanced receptor affinity of 5× over first generation mepyramine in an acidic pH (many acute inflammatory disease states are associated with acidosis, a low physiologic pH). Levocetirizine has a 24 hour receptor occupancy of ~75%, the highest of the commercially available antihistamines. Receptor occupancy of the second generation antihistamines appears to correlate with the pharmacodynamic activity in skin wheal and flare studies and with efficacy in allergen challenge chamber studies. Levocetirizine is approved in the US for the treatment of perennial allergic rhinitis and chronic idiopathic urticaria down to six months of age.

Levocetirizine has been objectively established as the most potent of the five modern generation antihistamines through histamine induced wheal and flare data. For example, levocetirizine at 5 mg per day is more effective than fexofenadine at its commonly prescribed dose of 180 mg per day in the United States. In Europe the adult dose is 120 mg per day. Levocetirizine has a lower volume of distribution, greater histamine receptor affinity in an inflamed state (low pH), and greater receptor occupancy at 24 hours at physiologic doses than fexofenadine. The corresponding values are shown in Table I.

TABLE I

COMPARISON BETWEEN FEXOFENADINE AND LEVOCETIRIZINE

|  | Fexofenadine | Levocetirizine |
|---|---|---|
| Vd-L/kg | 5.6 L/kg | 0.4 L/kg |
| Receptor affinity in an acidic ph | increased 2x | increased 5x |
| Histamine receptor occupancy at 24 hours | ~25% | ~75% |
| Steady-state level | 3 days | 40 hours |

Levocetirizine decreases human rhinovirus titers in vitro by log-2. Not to be bound by a particular theory, the cellular mechanism of action is a proposed reduction of the activation of the intracellular protein complex NF-kB (nuclear factor kappa B) which is in turn responsible for the reduction of I-CAM-1. I-CAM-1, a transmembrane protein, is viewed as the portal of entry of human rhinovirus into the cell. Rhinovirus can be found in ~50% of cases of acute asthma and is responsible for 30-50% cases of the 'common cold.' A one-log reduction in viral titers has been independently determined to correlate with improved symptoms. In addition, levocetirizine has been shown to decrease eosinophil migration and decrease inflammatory mediators, IL-4, IL-6, and IL-8. IL-6, a signaling protein, regulates in part: fever, the body's response to trauma, and the acute (immediate) phase of the allergic reaction.

Montelukast, a leukotriene receptor antagonist, acts by binding with high affinity and selectivity to the CysLT1 receptor to inhibit the physiologic actions of the leukotriene LTD4. Leukotrienes are fatty signaling molecules whose effects include airway edema, smooth muscle contraction and altered cellular activity associated with the inflammatory process. Overproduction of leukotriene is a major cause of inflammation in asthma and allergic rhinitis. The cysteinyl leukotrienes (LTC4, LTD4, LDE4) are products of arachidonic acid metabolism. These leukotrienes are released from various cells including mast cells and eosinophils. They bind to receptors in the human airway and on other pro-inflammatory cells including eosinophils and certain myeloid stem cells. The cysteinyl leukotrienes have been correlated with the pathophysiology of asthma and allergic rhinitis.

Leukotriene D4 is the most potent of the cysteinyl leukotrienes in contracting airway smooth muscle. Leukotriene receptors, such as $CysLT_1$, are found throughout the cells of the respiratory tree (including airway smooth muscle cells and airway macrophages) as well as on other pro-inflammatory cells in the body, particularly eosinophils and certain myeloid stem cells. Leukotrienes also function to promote the recruitment of eosinophils, dendritic cells and T cells. Eosinophil infiltration is considered by some authorities as a hallmark of inflammation.

Montelukast is FDA approved in the US for the treatment of perennial allergic rhinitis, asthma, seasonal allergic rhinitis, and exercised induced bronchospasm. Montelukast has been shown to be ineffective in improving asthma control or cold symptom scores caused by experimental rhinovirus infection. See Kloepfer K M, et al., Effects of montelukast in patients with asthma after experimental inoculation with human rhinovirus 16. Annals Allergy Asthma Immunology. 2011; 106:252-257. Unlike levocetirizine, no decrease in viral shedding was observed in rhinovirus-infected individuals treated with montelukast and there was no significant difference in reported cold symptom scores compared to placebo-treated individuals. Analysis of secondary outcomes suggests that montelukast may protect against reductions in lung function and increases in sputum eosinophils caused by common cold infections. During the recovery phase the percentage of sputum eosinophils was elevated in the placebo group, while the montelukast group remained at baseline levels. Further, peak expiratory flow was not decreased in the montelukast-treated patients. Other studies have shown that montelukast treatment has no effect on the respiratory symptoms of patients with acute respiratory syncitial virus bronchiolitis. See Bisgaard, H., et al., Study of montelukast for the treatment of respiratory symptoms of post-respiratory syncitial virus bronchiolitis in children, Am. J. Respir. Crit. Care Med., 2008; 178:854-860; and Proesmans, M., et al., Montelukast does not prevent reactive airway disease in young children hospitalized for RSV bronchiolitis, Acta Paediatr. 2009; 98:1830-34. However, some studies indicate that treatment with montelukast reduced the number of days with worsened asthma symptoms and unscheduled doctor's visits in children with mild allergic asthma and resulted in a modest reduction of symptoms in children with recurrent wheezing when given at the first sign of upper respiratory tract illness. See Sears, M. R. and Johnston, N.W., Understanding the September asthma epidemic. J. Allergy Clin. Immunol. 2007; 120:526-29; Bacharier, L. B., et al., Episodic use of an inhaled corticosteroid or leukotriene receptor antagonist in preschool children with moderate-to-severe intermittent wheezing. J. Allergy Clin. Immunol. 2008; 122:1127-35.

Montelukast reaches a steady state level, like the second generation antihistamine, levocetirizine, in less than two days. Unlike other currently available leukotriene modulators, zileuton and zafirlukast, routine monitoring of liver function tests is not required. There are no drug interactions with warfarin, theophylline, digoxin, terfenadine, oral contraceptives, or prednisone.

The two molecules are safe, i.e., FDA approved in the United States for allergic disorders down to age six months. They can be given primarily or in conjunction with many of the existing therapeutic protocols for the treatment of inflammation, including but not limited to, influenza, acute asthma and the common cold. Both medications are pregnancy category B (Table II).

TABLE II

PREGNANCY CATEGORY DEFINITIONS

| Category | Definition | Explanation |
| --- | --- | --- |
| A | Generally acceptable | Controlled studies in pregnant women show no evidence of fetal risk. |
| B | May be acceptable | Either animal studies show no risk but human studies not available or animal showed minor risks and human studies were done and showed no risk. |
| C | Use with caution if benefits outweigh risks | Animal studies show risk and human studies not available or neither animal nor human studies were done. |
| D | Use in life-threatening emergencies when no safer drug is available | Positive evidence of human fetal risk. |
| X | Do not use in pregnancy | Risks involved outweigh potential benefits. Safer alternatives exist. |

Existing treatment of inflammation focuses on the underlying condition and nature of the presentation. Commonly employed are a myriad of agents such as: diphenhydramine (Benadryl®), oxygen, epinephrine, steroids, beta-agonists, non-steroidal anti-inflammatory agents (NSAIDS), antipyretics, antibiotics, antifungals, and antivirals. Paradoxically, the commonly employed NSAIDS actually increase the production of leukotrienes.

Steroids, which are widely used to treat inflammation, have significant short and long-term side-effects (Table III). With regard to treating inflammation associated with rhinosinusitis, nasal steroids have their limitations, particularly in the elderly and those patients on aspirin, clopidogrel or warfarin prescribed to reduce the risk of stroke and heart attack. Even in patients who do not take these traditional "blood thinners," the risk of spontaneous epistaxis from nasal steroid sprays is between 4-22%. The risk of epistaxis is medication dependent. Epistaxis is a significant consideration in many patients 55 or older.

TABLE III

STEROID SIDE EFFECTS

| Short term | Long term |
|---|---|
| Increased propensity for opportunistic infection | Glaucoma |
| Increased blood pressure | Cataracts |
| Mood changes | High-blood pressure |
| Increased blood sugar | Heart disease |
| Increased intraocular pressure | Diabetes mellitus |
| Water retention | Obesity |
| Weight gain | Acid reflux/GERD |
| Increased risk for congestive heart failure | Osteoporosis |
| Flushing | Myopathy |
| Increased appetite | Increased propensity for opportunistic infection |
| Insomnia | Cushing syndrome |

The typical daily dosage for levocetirizine is 5 mg for adults, and levocetirizine exhibits the following advantageous properties: i) Short time to reach peak plasma levels—0.9 hr; ii) Short time to steady state level—40 hrs; iii) Low volume of distribution (goes directly to the target receptor); iv) High receptor occupancy at 24 hours 75%; v) Increased receptor affinity in inflamed tissue (acidic pH; up to 5× that of first generation molecules); vi) Pregnancy category B; vii) FDA approved down to six months for other disease states, i.e., perennial allergic rhinitis and chronic idiopathic urticaria; viii) Anti-inflammatory properties; and ix) Anti-viral properties. Studies in humans have shown that doses of levocetirizine up to 30 mg/day can be safely administered.

Montelukast, a leukotriene receptor antagonist, acts concurrently to protect the respiratory tree as well as block mediators in the inflammatory cascade. The typical daily dosage of montelukast is 10 mg for adults, and montelukast exhibits the following advantageous properties: i) montelukast is a selective receptor antagonist, inhibiting the physiologic action of LTD4 at the CysLTi receptor; ii) montelukast binds with high affinity and selectivity to the CysLTi receptor without producing any agonist activity; iii) montelukast is rapidly absorbed; iv) montelukast reaches a peak plasma concentration in 3-4 hours; v) the oral bioavailability and Cmax of montelukast are not affected by a standard meal; vi) montelukast has a linear pharmacokinetics to 50 mg; vii) doses as low as 5 mg in adults cause substantial blockage of LTD4-induced bronchoconstriction; viii) in a placebo controlled crossover study, montelukast inhibited early-phase bronchoconstriction due to antigen challenge by 75%; ix) montelukast is FDA approved down to six months of age; and x) montelukast has no drug interactions with warfarin, theophylline, digoxin, terfenadine, oral contraceptives, or prednisone. Montelukast has been administered at doses up to 200 mg/day to adult patients for 22 weeks and in short-term studies, and up to 900 mg/day to patients for approximately one week without clinically important adverse experiences.

Accordingly, both levocetirizine and montelukast are pregnancy category B in the United States and are FDA approved in the United States down to six months of age for other disease processes. Moreover, both drugs have only once daily dosing, and no routine monitoring of blood work is necessary for most clinical situations. Further, both drugs exhibit minimal clinically relevant interactions with other medications. As described herein, both levocetirizine and montelukast administered orally reach steady state levels within two days to rapidly produce a synergistic and complementary anti-inflammatory effect.

Administration of montelukast and a second generation antihistamine, fexofenadine, has a synergistic effect in the treatment of allergic rhinitis. Allergic rhinitis, also known as pollenosis or hay fever, is an allergic inflammation of the nasal airways which occurs when an allergen such as pollen or dust is inhaled by an individual with a genetically susceptible immune system (estimated at >20 percent of the population). The allergen triggers antibody production, a serum specific immunoglobulin E (IgE), which in turn can bind to mast cells and basophils containing histamine. Upon re-exposure to the offending antigen, histamine is released causing the itching, swelling, and mucus production which are well known to seasonal allergy sufferers. A combination of montelukast and fexofenadine reduced nasal congestion both subjectively, using patient diary and VAS evaluations, and objectively, using rhinomanometry and physical examination, with statistical significance compared to fexofenadine alone or fexofenadine with placebo.

However, the scientific literature does not clearly indicate whether the combination of an antihistamine plus a leukotriene offers an advantage over each alone for treatment in general. For example, in one chronic inflammatory disease state, chronic idiopathic urticaria, montelukast did not appear to offer an advantage over the second generation antihistamine desloratadine. See DiLorenzo G, et. al. Randomized placebo-controlled trial comparing desloratadine and montelukast in combined therapy for chronic idiopathic urticaria. J Allergy Clin Immunol 2004; 114-:619-25. Further, the FDA in April 2008 did approve the combination of loratadine, also a second generation antihistamine, and montelukast for the treatment of allergic rhinitis and asthma, finding no benefit from a combined pill.

Here, we describe the unexpected synergistic effects of combining levocetirizine and montelukast. Not wishing to be bound by a particular theory, a detailed examination of the pharmacokinetics of levocetirizine at the cell level illuminates the unique inflammatory properties that extend beyond the IgE mediated release of histamine. Levocetirizine exhibits a low volume of distribution (0.4 L/kg), prolonged dissolution time from the H1 receptor in an acidic ph, enhanced receptor affinity as a pure isomer of cetirizine, and the highest receptor occupancy at 24 hours of any currently available antihistamine. Such parameters impart an inflammatory effect by down regulating IL-4, IL-6, IL-8 as well as cellular adhesion molecules. The latter are a homogeneous group of inducible immunoglobulins, integrins and selectins involved in cell-to-cell adhesion, cellular recruitment, homing and healing. In addition levocetirizine has been shown in vivo to decrease ICAM-1, IL-6, IL-8, TLR3 expression and NF-kappa B activation resulting in decreased human rhinovirus titers by log-2. Many rhinovirus serotypes share the same cellular receptor identifying ICAM-1 as the portal of entry into the cell. Levocetirizine inhibits rhinovirus-induced ICAM-1 and cytokine expression and viral replication in airway epithelial cells. One log reduction in viral shedding results in a significant clinical benefit in HRV-infected (human rhinovirus) patients.

An unmet clinical need arose in 2009 with the H1N1 pandemic. The primary drug of choice for influenza, oseltamivir, did not appear to reduce influenza related lower respiratory tract complications. For neuraminidase inhibitors, there was a shortening of the illness by only one half to one day, which indicated that neuraminidase inhibitors do not prevent infection or stop nasal viral excretion, and therefore may be a suboptimal means of interrupting viral spread in a pandemic. Moreover, during this time frame, California reported alarming data on the severity of H1N1 influenza in pregnant and postpartum women, i.e., from April 23 through Aug. 11, 2009 22% of pregnant or postpartum women required intensive care for the treatment of H1N1 and 8% died. Clinically it was demonstrated that the combination of levocetirizine plus montelukast (the latter added to protect the lower airway; both of which were Pregnancy Category B), could be safely and effectively used to ameliorate/shorten the course of influenza.

Not wishing to be bound by a particular theory, the steroid model suggests that levocetirizine acts in a non-IgE-mediated capacity at the level of NF-kB (See FIG. 1) whereas montelukast acts at the CysLT1 receptor to inhibit the physiologic actions of LTD4. Both molecules are known to reduce the quantity of eosinophils or their migration to site of inflammation. Montelukast, in addition, also decreases the recruitment of dendritic cells and T cells.

The actions of levocetirizine plus montelukast surpass the individual physiologic mechanisms of each, well beyond the treatment of allergic rhinitis and asthma. At least in part, it is the anti-viral and anti-inflammatory properties of levocetirizine vis-a-vis nuclear factor kB; the inhibition of the actions of LTD4 by montelukast, underscored by ability of both levocetirizine and montelukast to inhibit the eosinophil quantity/migration, which impart synergy. This synergy is reflected by significantly improved clinical outcomes in a myriad of acute and chronic inflammatory disease states.

Embodiments described herein relate to methods of treating inflammation of the entire respiratory tree, including in part, the nose and paranasal sinuses known as rhinosinusitis with montelukast and levocetirizine. Rhinosinusitis considered on a timeline may be acute, with a duration of less than six weeks (usually 4-6 weeks), subacute, having a duration of six to twelve weeks, or chronic, having a duration of greater than or equal to twelve weeks. Acute rhinosinusitis may be precipitated by multiple factors not limited to chemical irritation, trauma, allergic rhinitis or an earlier upper respiratory tract infection, which may be bacterial, viral, or, less commonly, fungal in origin. The most common causative agents of acute sinusitis of bacterial origin are *Streptococcus pneumoniae, Haemophilus influenzae, Moraxella catarrhalis, Staphylococcus aureus*, other streptococci species, anaerobic bacteria, and, less commonly, gram negative bacteria. Bacterial sinusitis tends to be more persistent than viral rhinosinusitis, i.e., the common cold, which typically lasts for 7 to 10 days.

Several embodiments described herein relate to the treatment of acute rhinosinusitis caused by a viral or bacterial infection with montelukast and levocetirizine. In some embodiments, montelukast and levocetirizine are taken prophylactically to prevent a viral respiratory tract infection from escalating to an acute, often opportunistic, secondary bacterial sinusitis, bronchitis and/or pneumonia. In some embodiments, montelukast and levocetirizine are administered immediately, one hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, and/or 30 days after exposure to the pathogens (virus, bacteria, fungi, etc.). Several embodiments relate to the treatment of patients with clinical manifestations of influenza with montelukast and levocetirizine. In some embodiments, montelukast and levocetirizine treatment reduces the duration of influenza. In some embodiments, montelukast and levocetirizine treatment reduces the severity of influenza symptoms. Several embodiments relate to the treatment of patients with clinical manifestations of the common cold with montelukast and levocetirizine. In some embodiments, montelukast and levocetirizine treatment reduces the duration of the cold. In some embodiments, montelukast and levocetirizine treatment reduces the severity of cold symptoms.

Chronic rhinosinusitis is an inflammatory condition/disease of the nose and paranasal sinuses lasting for greater than or equal to twelve weeks. Symptoms include in part, any combination of nasal congestion, facial pain, headache, coughing, an increase in asthma symptoms, malaise, discharge, feeling of facial tightness, dizziness, and/or aching teeth. Rhinosinusitis in general can be categorized into four categories: (1) acute bacterial rhinosinusitis (ABRS), (2) chronic rhinosinusitis without nasal polyposis (CRSsNP), (3) chronic sinusitis with nasal polyposis (CRSwNP), and (4) allergic fungal rhinosinusitis (AFRS). See Meltzer, EO. Rhinosinusitis: Developing guidance for clinical trials. J Allergy Clin Immunol 2006 November; S20. Nasal polyposis is a subgroup of chronic rhinosinusitis in which the inflammation of the nose is associated with two or more of the following signs and symptoms: nasal obstruction or congestion, nasal discharge, hyposmia or anosmia, facial pain or feeling of pressure, endoscopic evidence of polyps or mucopurulent discharge from middle meatus with or without edema or mucosal obstruction of the meatus and CT images which show mucosal changes of osteomeatal complex or paranasal sinuses. See Fokkens W, et. al. EAACI position paper on rhinosinusitis and nasal polyps executive summary. Allergy, 2005; 60, 583-601., Fokkens, W, et. al. European Position Paper on Rhinosinusitis and Nasal Polyps group (2007) European position paper on rhinosinusitis and nasal polyps. Rhinology 2007; 20, 1-136. Conventional treatment for chronic rhinosinusitis often involves functional endoscopic sinus surgery, antibiotics, systemic and topical steroids, and to a much lesser extent an antihistamine or leukotriene modulator. The use of antihistamines in patients with only polyps has not been extensively studied. See Casale M, et. al. Nasal Polyposis: From Pathogenesis to Treatment, an Update. Inflammation & Allergy—Drug Targets 2011, 10, 158-163. Mometasone furoate monohydrate, a topical nasal steroid spray, is the only FDA approved medication in the United States for the treatment of nasal polyposis. The recommended dose is two squirts each nostril twice a day.

Embodiments described herein relate to the treatment of chronic rhinosinusitis with montelukast and levocetirizine. Several embodiments described herein relate to the treatment of nasal polyposis with montelukast and levocetirizine. In some embodiments, montelukast and levocetirizine treatment reduces the size and/or number of polyps. Some embodiments relate to the treatment of chronic rhinosinusitis with montelukast and levocetirizine in the absence of steroids, antibiotics or surgical treatment. In other embodiments, montelukast and levocetirizine are administered in conjunction with antibiotics and/or steroids and/or surgical treatment as deemed clinically applicable. The chronic rhinosinusitis treatment protocol with or without other treatment modalities is as follows:

TABLE IV

TREATMENT PROTOCOL FOR CHRONIC RHINOSINUSITIS

| Levocetirizine-US | |
|---|---|
| Adults: | 5 mg/day |
| Children: 6-11 years of age: | 2.5 mg/day |
| Children: 6 months to 5 years | 1.25 mg/day |
| Montelukast-US | |
| Adults: | 10 mg orally/day |
| Children 6-14 years of age: | 5 mg orally/day |
| Children 6 months-5 years of age: | 4 mg orally/day |

Patients may be seen at least quarterly in the office with endoscopic review of the nose/paranasal sinuses when clinically appropriate. A pretreatment and follow-up CT scan of the perinasal sinuses at 6 months to one year post initiation of therapy may be performed to provide objective data on which to tailor existing medical therapy.

Several embodiments relate to a method of treating rhinitis with montelukast and levocetirizine. Rhinitis, inflammation of the nasal passages, is commonly caused by a viral or bacterial infection, including the common cold, the latter of which is caused primarily by Rhinoviruses and Coronaviruses. See Eccles R. Understanding the Symptoms of the Common Cold and Influenza. Lancet Infectious Diseases 2005; 5(11): 718-725. Rhinitis is categorized as: (i) infective rhinitis; (ii) nonallergic rhinitis; and (iii) allergic rhinitis. Several embodiments relate to a method of treating infective rhinitis with montelukast and levocetirizine. Some embodiments relate to a method of treating nonallergic rhinitis with montelukast and levocetirizine. Some embodiments relate to a method of treating allergic rhinitis with montelukast and levocetirizine.

Several embodiments described herein relate to the treatment of chronic rhinosinusitis with montelukast and levocetirizine. Some embodiments, relate to the treatment of chronic rhinosinusitis with montelukast and levocetirizine in the absence of steroid or antibiotic treatment. In other embodiments, montelukast and levocetirizine are administered in conjunction with antibiotics and/or steroids.

Several embodiments relate to a method of treating non-IgE-based inflammation with montelukast and levocetirizine.

Several embodiments relate to a method of treating combined IgE and non-IgE-mediated inflammation with montelukast and levocetirizine.

The following Table V shows the existing country guidelines for dosages in the treatment of allergic disorders.

TABLE V

GUIDELINES FOR DOSAGES IN THE TREATMENT OF ALLERGIC DISORDERS

| Levocetirizine-US | |
|---|---|
| Adults: | 5 mg/day |
| Adults: | 10 mg orally/day |

TABLE V-continued

GUIDELINES FOR DOSAGES IN THE TREATMENT OF ALLERGIC DISORDERS

| Children: 6-11 years of age: | 2.5 mg/day |
|---|---|
| Children: 6 months to 5 years | 1.25 mg/day |
| Montelukast-US | |
| Children 6-14 years of age: | 5 mg orally/day |
| Children 6 months-5 years of age: | 4 mg orally/day |

Several embodiments relate to the use of a combination of levocetirizine and montelukast to treat a bacterial infection. Examples of bacterial infections that may be treated by a combination of levocetirizine and montelukast include, but are not limited to, acute bacterial rhinosinusitis (ABRS). In some embodiments, levocetirizine and montelukast may be administered with an antibiotic as determined by local presentation.

Several embodiments relate to the use of a combination of levocetirizine and montelukast to treat otitis media with effusion and associated ear disorders such as chronic mastoiditis and eustachian tube dysfunction (the auditory tube leading from the back of the nose to the middle ear). In some embodiments, levocetirizine and montelukast may be administered with antibiotics to treat for example, acute otitis media with purulent middle ear effusion. In some embodiments, levocetirizine and montelukast may be administered without antibiotics to treat chronic middle ear effusion, for example, chronic otitis media. In some embodiments, levocetirizine and montelukast may be administered with other treatment modalities such as, but not limited to, steroids and/or antiviral agents.

Several embodiments relate to the use of a combination of levocetirizine and montelukast to treat allergic fungal rhinosinusitis (AFRS). In some embodiments, levocetirizine and montelukast may be administered with other treatment modalities such as, but not limited to, steroids and/or an antifungal agent.

Intravenous therapy of levocetirizine and montelukast, the latter currently under investigation in the United States, would enhance the individual and combined clinical response presently seen with the administration of oral medication. The IV montelukast plasma concentration area under the curve profile, 7 mg, is comparable to the approved 10 mg oral montelukast tablet. The former has been shown in acute asthmatics to significantly improve FEV1 (forced expiratory volume at one sec) at 10 minutes when compared with placebo.

Accordingly, the dosing for acute inflammation could be daily as delineated above individually in the same setting, as a dual-layer tablet(s), and/or as a blister pack containing both medications for a 10 day course of therapy. For a moderate to severe clinical presentation, the levocetirizine component can be given at time zero (5 mg), 12 hours (5 mg) and 24 hours (5 mg), during the first 24 hour day, in order to achieve a steady state level of the molecule in less than 40 hours. Levocetirizine human dosing safety studies have been performed at up to 30 mg/day. Sedation is the principal side effect experienced at higher doses. Independent research has shown that levocetirizine alone can be dosed at 20 mg/day to treat severe cases of idiopathic urticaria.

The application for the combination of levocetirizine and montelukast includes, but is not limited to treating, ameliorating, or preventing the following symptoms. For Influenza, the combination can be useful to shorten the course of seasonal flu and prevent or minimize the development of lower respiratory tract infections/complications, and/or to establish an improved, safe, world-wide protocol for influenza prior to the next pandemic, e.g., H5N1 with its associated 50% mortality rate. For upper respiratory tract infections, not limited to rhinovirus, the combination can be useful to limit the infection itself, and/or to prevent or reduce the potential development of secondary sinusitis, bronchitis and pneumonia. The combination can be useful for treatment of Ebstein-Barr Virus, particularly, but not limited to those patients with respiratory involvement.

For acute asthma in conjunction with existing protocols, not limited to exacerbations caused by rhinovirus (~50% of cases), the combination can be useful to shorten the course of the event, reduce hospitalizations and death. The combination can be useful for pre-treatment of patients allergic to one or more classes of antibiotics requiring antimicrobial therapy. These patients are at risk, 4-10× over the general population, of developing a subsequent ALE (allergic-like event). For patients with moderate to severe life-threatening disease requiring dual/triple antibiotics, the combination can be useful to reduce the probability of developing a side-effect(s) from the primary treatment medications. The combination can be useful during and following radiation therapy to ameliorate the inflammatory response. The combination can be useful for patients requiring steroids for the treatment of inflammation who are otherwise at increased risk for the development of steroid induced complications. Examples include but are not limited to the following: i) A severe insulin dependent diabetic with an infection such as facial paralysis, and ii) Patient with latent Tuberculosis. For patients on antiviral medication for acute disease, the combination can be used to prevent complications related to the medication(s) as well as complications associated with the disease process itself. The combination can be used to treat serum sickness, with or without steroids. For pre-treatment of patients on immunotherapy, the combination can be used to prevent or ameliorate the risk of a systemic reaction. Examples of high risk patients with the potential to develop a life-threatening, systemic event include but are not limited to severe asthmatics, those patients with a concurrent respiratory tract infection, and those patients with a prior history of a systemic reaction. For pre and intra-treatment of those patients on chemotherapy, the combination can be used to ameliorate side effects associated with the administration of chemotherapeutic drug(s). For patients exhibiting a transfusion reaction, the combination can be used to limit the side effects/life threatening event during the initial reaction and in preparation for any requisite subsequent transfusion.

As will be readily apparent to one skilled in the art, the useful in vivo dosage of levocetirizine and montelukast to be administered and the particular mode of administration will vary depending upon the age, weight, medical condition of the patient, the severity of the condition to be treated, the route of administration, the renal and hepatic function of the patient, and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Advantageously, compounds of the present embodiments may be administered, for example, in a single daily dose, or the total daily dosage may be administered in divided doses of two, three or four times daily.

TABLE VI

TREATMENT PROTOCOL FOR ACUTE INFLAMMATION NOT LIMITED TO INFLUENZA AND THE COMMON COLD

| Levocetirizine-US | |
|---|---|
| Adults: | 5 mg/day |
| Children: 6-11 years of age: | 2.5 mg/day |
| Children: 6 months to 5 years | 1.25 mg/day |
| Montelukast-US | |
| Adults: | 10 mg orally/day |
| Children 6-14 years of age: | 5 mg orally/day |
| Children 6 months-5 years of age: | 4 mg orally/day |

Depending upon the severity of the acute process, the doses in Table VI can be modified. For example, the age appropriate dose for levocetirizine may be given at time zero (at presentation) with an additional age appropriate dose at 12 hours. In order to protect the lower airway, particularly in the face of bronchitis/pneumonia, a dose of montelukast may be given at time zero (at presentation) with an additional age appropriate dose of montelukast at 12 hours. In this fashion the steady state level of the two drugs would approach 24 hours. Montelukast, like levocetirizine, is considered a very safe molecule. Montelukast has been administered at doses up to 200 mg/day (20× the standard adult daily dose) to adult patients for 22 weeks and in short-term studies, up to 900 mg/day (90× the standard adult daily dose) to patients for approximately one week without clinically important adverse events. Dosing duration may parallel the generally accepted protocols for their respective disease states. For example, conventional therapy for an acute infectious disease process is typically administered for 5-14 days. A course of combined levocetirizine once daily plus montelukast once daily may be given for the same duration. For the treatment of chronic inflammatory disease states, an age appropriate once daily dosing of each medication may also be administered.

Autoimmune Disorders

Several embodiments relate to the use of a combination of levocetirizine and montelukast for the treatment of autoimmune disorders.

Autoimmunity is described as an immune response directed against an antigen within the body of the host. This definition is independent of whether the response is innate or acquired, and if acquired, whether it is induced by a foreign or autochthonous antigen. In other words, if acquired, the response is induced by a foreign antigen or antigen found in the part of the body or locality in which it originates, such as that produced by a cancer. Autoimmunity usually involves both T-cell and B-cell responses in a three dimensional complex immunologic array. The primary requirement is an immune response directed to a self-antigen.

In dealing with human disease it is often difficult to establish causality. As such the diagnosis of an autoimmune disease may be established by direct evidence, indirect evidence or circumstantial evidence.

Direct evidence usually involves the transfer of an antibody from a patient to a healthy recipient. Examples are the reproduction of the disease pemphigus by injection of patient serum into a neonatal mouth or human-to-human transfer of an autoantibody from the transplacental migration of the disease, e.g., Grave's disease, myasthenia gravis, and neonatal lupus.

Indirect evidence can be found in such disease states as: (a) the reproduction of disease in animals via immunization with a select antigen, (b) naturally occurring disease in animals resembling the human counterpart, and (c) disease created by manipulating the immune system.

Circumstantial evidence, the lowest level of proof, is suggested by confirming the presence of autoantibodies. Another type of circumstantial evidence is identified from the finding that autoimmune diseases have a tendency to cluster, likely from defined or yet to be defined genetic susceptibility traits.

From a pathological perspective, with few exceptions all autoimmune diseases require the presence of self-reactive CD4 T lymphocytes (Table VII).

TABLE VII

PARTIAL LIST OF AUTOIMMUNE DISEASES

| Disease | Main organ affected | Proposed self-antigen(s) | Clinical presentation |
|---|---|---|---|
| Organ-specific autoimmune diseases ||||
| Multiple sclerosis | Central nervous system | Myelin basic protein, myelin oligodendrocyte protein | Loss of vision, weakness of limbs, sensory abnormalities, incontinence |
| Sympathetic ophthalmia | Eye | Various uveal antigens | Eye pain, loss of vision, sensitivity to light |
| Graves' disease | Thyroid | Thyrotropin receptor | Hyperthyroidism (weight loss, nervousness, palpitations, diarrhea), exophthalmos |
| Hashimoto's thyroiditis | Thyroid | Thyroperoxidase, thyroglobulin | Hypothyroidism (weight gain, constipation, skin changes, myxedematous dementia) |
| Goodpasture's syndrome | Lung, kidney | Glomerular basement membrane (type IV collagen) | Kidney and respiratory insufficiency |
| Pernicious anemia | Stomach | Intrinsic factor | Anemia, gastritis |
| Crohn's disease* | Intestine | ? microbial antigens | Hemorrhagic diarrhea, abdominal pain, draining fistulas |
| Ulcerative colitis* | Large Intestine | ? microbial antigens | Hemorrhagic diarrhea, abdominal pain |
| Diabetes mellitus type I | Pancreas | Islet cell, insulin, glutamic acid decarboxylase (GAD) | Polyphagia, polyuria, polydipsia, weight loss |
| Immune thrombocytopenia | Platelets | Glycoproteins on the surface of platelets | Easy bruising, hemorrhage |
| Myasthenia gravis | Muscle | Acetylcholine receptor | Muscle weakness, fatigability |
| Hemolytic anemia | Red cells | I antigen | Anemia |
| Systemic autoimmune diseases ||||
| Sjögren's syndrome | Salivary and lacrimal glands | Nuclear antigens (SSA, SSB) | Dry eyes, dry mouth, lung and kidney disease |
| Rheumatoid arthritis | Joints, lung, nerves | Citrulinated peptides in the joint, IgG | Deforming arthritis, skin nodules, occasional lung and nerve involvement |
| Wegener's granulomatosis | Lung, kidney | Proteinase 3 (c-ANCA) | Sinusitis, shortness of breath, kidney failure |
| Systemic lupus erythematosus | Kidney, skin, joints, central nervous system | DNA, histones, ribonucleoproteins | Arthritis, skin rashes, kidney insufficiency, nerve damage |

*Although previously considered autoimmune diseases, more recent evidence supports that they are autoinflammatory disorders.

A separate category of autoimmune diseases, the autoinflammatory diseases, exists in which there is no evidence of adaptive immunity in the form of self-reactive T cells. This latter group consists of a core of six disorders known as hereditary recurrent fever syndromes. The primary differences between the two major categories are reviewed in Table VIII.

TABLE VIII

COMPARISON OF AUTOIMMUNE AND AUTOINFLAMMATORY DISEASES

| Distinguishing feature | Autoimmune diseases | Autoinflammatory diseases |
|---|---|---|
| Arm of immunity affected | Adaptive immunity | Innate immunity |
| Genetic basis | Monogenic and polygenic disorders of adaptive immune function | Monogenic and polygenic disorders of innate immune function |
| Specific dysregulated component | Primary dysregulation of classical MHC-based, antigen-dependent T cell responses | Primary dysregulation of innate immune system processing and secretion of pro-inflammatory cytokines, IL-1$\beta$, IL-18, and others |
|  | Resultant secondary contribution of inflammatory responses | Resultant primary contribution of inflammatory responses |
| Effector mechanisms involved | Injury mediated by activation of CD4 subpopulations (Th1, Th2, Th17, and Treg) together with other innate effector cells (macrophages, mediator cells, NK cells via cytokine production) | The pathological abnormality in autoinflammatory diseases is a failure to control processing and secretion of IL-1$\beta$ and other pro-inflammatory cytokines in patients with these diseases |
|  | Tissue destruction, mediated directly by cytotoxic CD8 T cells |  |
|  | T cell-dependent B cell autoantibody production |  |
| Examples of diseases | Organ-specific autoimmune diseases | Familial Mediterranean fever |
|  | (Celiac disease, Graves' disease, type 1 diabetes, Addison's disease, autoimmune thyroiditis) | Neonatal-onset multiple system inflammatory disease |
|  | Systemic autoimmune diseases (SLE, RA) | Systemic-onset juvenile idiopathic arthritis (JIA) |
| Predominant symptoms | Fever | Fever |
|  | Maculopapular rash | Urticarial rash |
|  | Joint involvement (arthritis or arthralgias) | Pyogenic arthritis |
|  | Specific organ involvement | Pyoderma gangrenosum |

The provisional molecular/functional classification of the autoinflammatory diseases is outlined in Table IX.

TABLE IX

PROVISIONAL MOLECULAR/FUNCTIONAL CLASSIFICATION OF AUTOINFLAMMATORY DISEASES

| Disease | Example of disease | Gene/(chromosome)/product |
|---|---|---|
| Type 1: IL-1$\beta$ activation disorders (inflammasomopathies) |  |  |
| Intrinsic | Familial cold autoimmune syndrome (FCAS) | NLRP3/CIAS1 (1q44) |
|  | NOMID/CINCA |  |
|  | Muckle Wells |  |
| Extrinsic | FMF | MEFV (16p13.3)/pyrin (marenostrin) |
|  | PAPA | PSTPIP1 (15q24-25.1) |
|  | DIRA | IL1RN/IL1Ra |
|  | CRMO/SAPHO, | Complex |
|  | HIDS | MVK (12q24)/mevalonate kinase |

TABLE IX-continued

PROVISIONAL MOLECULAR/FUNCTIONAL CLASSIFICATION OF AUTOINFLAMMATORY DISEASES

| Disease | Example of disease | Gene/(chromosome)/product |
|---|---|---|
| Acquired or complex | Gout | Complex/uric acid |
| | Type 2 diabetes mellitus | Complex/hyperglycemia |
| | Fibrosing disorders (silicosis, asbestosis) | Complex/asbestos and silica |
| Type 2: NF-κB activation disorders | Crohn's disease | NOD2 (16p12)/NOD2(CARD15) |
| | Blau syndrome | NOD2 (16p12)/NOD2(CARD15) |
| | Familial cold autoimmune syndrome (FCAS2) | NLRP12 (19q13.4)/NRLP12(NALP12) |
| Type 3: Protein-folding disorders of the innate immune system | TNF receptor-associated periodic syndrome (TRAPS) | TNFRSF1A (12p13)/TNFR1 |
| | Spondyloarthropathies | Complex HLA-B (6p21.3)/HLA-B27 ERAP1 (5q15)/ERAP1 |
| Type 4: Complement disorders | Acquired hemolytic uremic syndrome (aHUS) | CFH (1q32)/Factor H MCP (1q32)/MCP (CD46) CFI (4q25)/Factor I CFB (6p21.3)/Factor B |
| | Age-related macular degeneration | CFH (1q32)/Factor H |
| Type 5: Cytokine-signaling disorders | Cherubism | SH3-binding protein 2/SH3-binding protein 2 |
| Type 6: Macrophage activation | Familial hemophagocytic lymphohistitiocytosis (HLH) | UNC13D (17q21.1)/Munc13-4 PRF1 (10q22)/Perforin 1 STX11 (6q24.2)/Syntaxin 11 Complex/virus |
| | Chediak-Higashi syndrome | LYST (1q42.3)/LYST (CHS1) |
| | Griscelli syndrome | RAB27A (15q21.3)/RAB27A |
| | X-linked lymphoproliferative syndrome | SH2D1A (Xq25)/SAP |
| | Hermansky-Pudlak syndrome | HPS1-8/HPS1-8 |
| | Secondary HLH | Complex |
| | Atherosclerosis | Complex/cholesterol |

Clinically, physicians tend to categorize autoimmune diseases as systemic (such as in the case of systemic lupus erythematosis) or organ-specific (such as type I diabetes mellitus). Therapy has generally been directed to the specific disease and associated presentation. Four therapeutic approaches are usually employed and are summarized in Table X.

TABLE X

THERAPEUTIC APPROACHES TO AUTOIMMUNE DISEASES

| | |
|---|---|
| Alteration of thresholds of immune activation | Blockade of costimulatory factors Antagonism of inflammatory cytokines or protective cytokines Inhibition of signaling cascades by small molecules |
| Modulation of antigen-specific cells | Induction of regulatory cells (intravenous, subcutaneous, or oral delivery of antigen) Alteration in peptide ligands Formation of complexes of peptide and major-histocompatibility-complex molecules Development of T-cell receptor vaccines Induction of B-cell tolerance Immune deviation from type 1 to type 2 helper T cells |

TABLE X-continued

THERAPEUTIC APPROACHES TO AUTOIMMUNE DISEASES

| | |
|---|---|
| Reconstitution of the immune system | Bone marrow ablation with autologous stem cells Bone marrow ablation with donor stem cells Bone marrow ablation without stem cells |
| Sparing of target organs | Antagonism of complement Antagonism of chemokines Use of antiinflammatory agents Inhibition of matrix metalloproteases Inhibition of nitric oxide synthase |

The complex causes of the two categories of autoimmune disorders offer considerable challenges to the development of new therapies. The combined synergy of levocetrizine plus montelulast in ameliorating the autoimmune/inflammatory response seen in many of these diseases offers significant promise without compromising existing or yet to be defined more directed therapy. Both molecules are considered Pregnancy Category B, i.e., the safest, and can be used to complement existing treatment regimens without inducing new problems. It is clinically held by many physicians, particularly the oncologists and rheumatologists, that many of the current modalities—such as the immunomodulators, immuonosuppressants, steroids, and intravenous gamma globulin, to name a few—precipitate side effects that are worse than the underlying disease.

Autoimmune Neutropenia

Neutropenia is defined as an absolute neutrophil count (ANC) of less than 1500/μL. The absolute count is equal to the product of the white blood cell count (WBC)× the fraction of combined polymorphonuclear cells plus band forms seen in the differential analysis. The lower the ANC, the higher the probability of significant infection, particularly below 1000/μL.

There is considerable overlap of the syndromes of autoimmune neutropenia, chronic idiopathic neutropenia, chronic benign neutropenia, and neutropenia of infancy in that they differ predominately in the age of presentation and duration of neutropenia. Neutropenia associated with immunodeficiency and isoimmune neonatal neutropenia are differentiated in that the source of the antibody is known. In the latter disease there is transplacental passage of IgG antibodies to neutrophil-specific antigens inherited from the father.

Difficulty is additionally founded in the fact that antineutrophil antibody testing is not readily available and if available, has a significant false negative rate. Moreover, management decisions are not based on antineutrophil antibody testing.

Therapy is directed to stabilize neutrophil levels at a reasonable level above the 1000 ANC range, usually by the use of steroids, or in the presence of actual or anticipated life threatening infection, by the administration of Neupogen® (filgrastim). Neupogen® acts by stimulating granulocyte and macrophage proliferation and differentiation; however, it is associated with serious reactions, such as splenic rupture, ARDS, thrombocytopenia, cutaneous vasculitis, and hemorrhage.

Immune Thrombocytopenia Purpura (Idiopathic Thrombocytopenia Purpura)

Immune thrombocytopenia purpura (ITP) is a common acquired bleeding disorder the diagnosis of which is satisfied by two criteria:
  (1) Isolated thrombocytopenia is present. The balance of the complete blood count is normal, unless otherwise coincidental abnormalities such as iron deficiency anemia are also present.
  (2) Clinically apparent associated conditions are not present on initial presentation. Examples of associated conditions are systemic lupus erythematosis, chronic lymphocytic leukemia, and antiphospholipid syndrome. Patients with these conditions are described as having secondary immune thrombocytopenia. Also drugs, including quinine containing beverages and herbal remedies are not apparent etiologies.

The laboratory diagnosis of ITP is compromised by the by the poor sensitivity (49-66%) of existing assays designed to measure platelet-bound antibodies.

The clinical manifestations vary from patient to patient, with bleeding ranging from petechiae and easy bruising to a severe bleeding diathesis. Among adults approximately 70 percent are women and 70 percent of these women are below 40 years of age. From a genetic perspective, HLA-DR4 and DRB1*0410 alleles in the ITP subpopulations have been associated with an unfavorable and favorable responses respectively, to corticosteroids, the mainstay of treatment. Moreover, HLA-DRB1*1501 has been linked to an unfavorable response to splenectomy, another common form of therapy.

Adults usually require treatment with prednisone at the time of presentation. Whereas platelet counts of 50,000 per $mm^3$ (normal 150,000-450,000 per $mm^3$) are usually discovered incidentally, petechiae or ecchymosis develop spontaneously when counts are between 10,000-30,000 per $mm^3$. There is a definite risk for internal bleeding when counts drop below 10,000 per $mm^3$. Another treatment modality involves the use of intravenous gamma globulin (IVGG), which yields an initial response in 80% of patients. That being said, sustained remission is infrequent and the cost of therapy is considerable.

Figure 3:
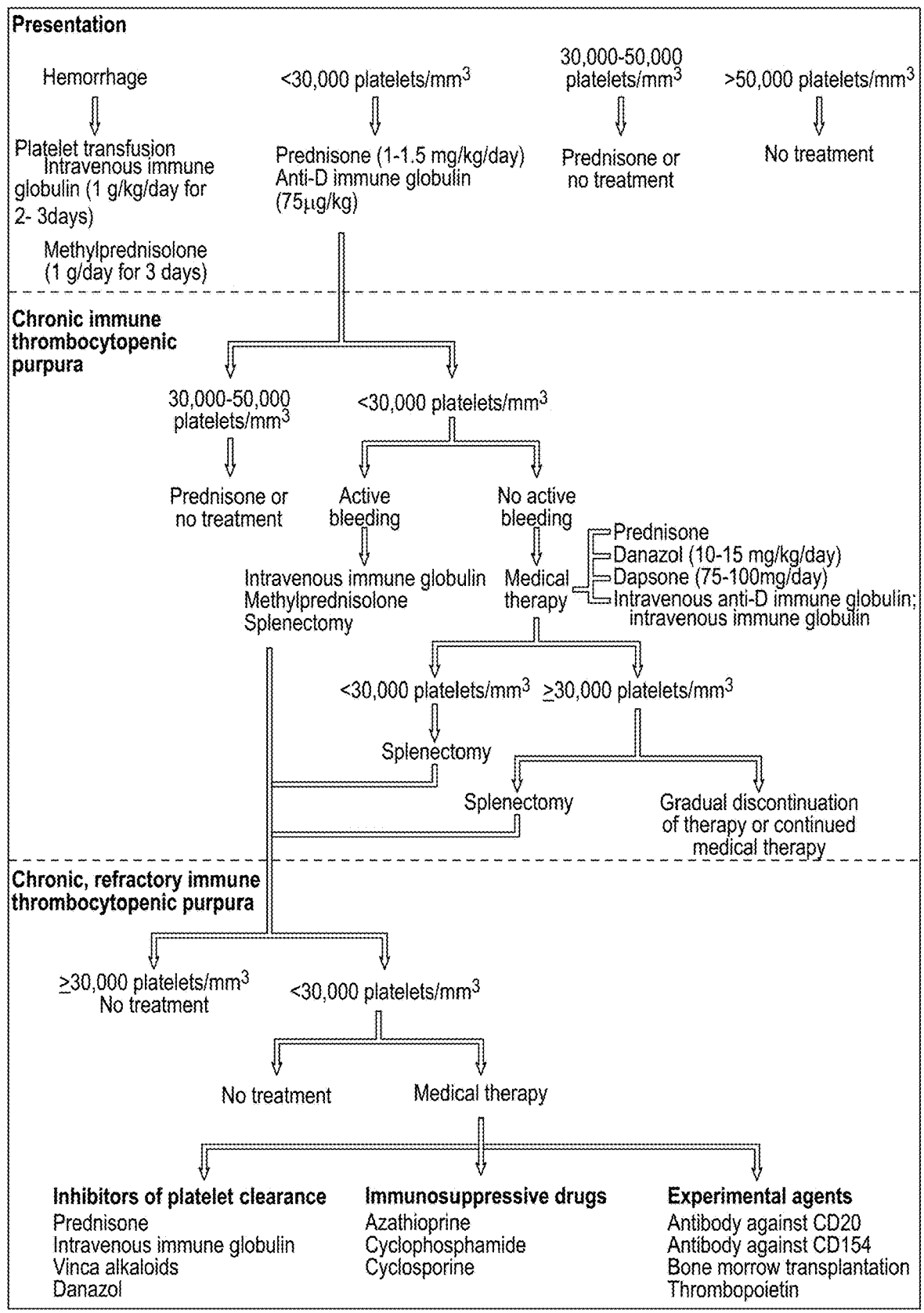
FIG. 3 shows a diagram of an Immune Thrombocytopenia Purpura Treatment Algorithm.

Splenectomy is offered as second line therapy following trials of prednisone, Danazol, Dapsone and IVGG. Chronic refractory ITP with platelets counts less than or equal to 30,000 per $mm^3$ include treatment options such as the vinca alkaloids, azathioprine, cyclophosphamide, cyclosporine, bone marrow transplantation and thrombopoietin. FIG. 3 shows a diagram of an Immune Thrombocytopenia Purpura Treatment Algorithm (Cines D B, Blanchette V S. Immune Thrombocytopenia Purpura. N Engl J Med 2002; 346: 995-1008, herein incorporated by reference in its entirety).

Administration of levocetirizine and montelukast in combination exhibits unexpectedly superior results in the treatment of autoimmune disorders. The combined use of levocetirizine plus montelukast offers a novel, safe and effective alternative to even first line prednisone. The combination of levocetirizine and montelukast act synergistically within the steroid pathway and without the associated steroid side effects. Moreover, administration of the combination of levocetirizine and montelukast can also have a sustained effect on a patient; for example, a patient's white blood cell count can be stabilized and maintained for at least several months and potentially several years.

The combination of levocetirizine and montelukast may be used as part of a prolonged treatment regimen. Furthermore, combinations of levocetirizine and montelukast can be used safely in conjunction with many existing treatment protocols. For example, glucocorticoids, such as prednisone or methylprednisolone, can be administered to a patient in combination with levocetirizine and montelukast. As another example, immunosuppressants, including but not limited to methotrexate, azathioprine, cyclophosphamimde, and cyclosporine, may also be administered to a patient in combination with levocetirizine and montelukast. Other typical therapeutic approaches used in the treatment of autoimmune diseases that can be combined with levocetirizine and montelukast include, but are not limited to, the use of inhibitors of platelet clearance (such as intravenous immune globulin; intravenous anti-D immune globulin, vinca alkaloids, and danazol), the use of experimental agents (such as antibodies against CD20 or CD154, bone marrow transplantation, and thrombopoetin), and splenectomy. In some embodiments, supplements, such as ferrous gluconate or vitamin C, can be administered to the patient along with the combination of levocetirizine and montelukast. The combination of levocetirizine and montelukast can also be used in conjunction with antibacterial agents, such as dapsone, or therapeutically active proteins, such as filgrastim. Additionally, the combination of levocetirizine and montelukast can be used with lenalidomide (Revlimid®), an immunomodulator.

In some embodiments, the combination of levocetirizine and montelukast may be used with lower dosages of existing therapies. For example, levocetirizine and montelukast can be used in patients otherwise refractory to traditional therapy to maintain safe clinical parameters, e.g. white blood cell counts, platelet counts, while on lower doses of steroids. They can also be used to facilitate a steroid taper as required by a significant clinical event such as sepsis.

A non-limiting example of a treatment protocol for use in a patient with, for example, immune thrombocytopenia purpura (ITP) post splenectomy complicated by sepsis can be as follows: With an infection resulting in a drop in the platelet count below 50,000/µL, e.g., sepsis, add steroids to the treatment regimen to stabilize the platelet count. Thereafter taper the steroids over one to two months. The duration of the steroid taper (from 60 mg of prednisone/day to zero) can be effectively foreshortened by adding levocetirizine 2.5-5 mg plus montelukast 5-10 mg orally in the morning for twice daily dosing. Once the counts have stabilized, the patient may resume their once daily dosing of levocetirizine and montelukast. Thus, maintenance therapy can consist of 5 mg of levocetirizine orally at night and 10 mg of montelukast orally at night.

Thus, the combination of levocetirizine and montelukast allows patients to use decreased dosages of steroids (also shown in Examples 1 and 2), which results in a decreased risk of developing an opportunistic infection, electrolyte imbalance, weight gain, fluid retention, cataract formation, hypertension, diabetes mellitus, and osteoporosis to iterate just a few of the myriad of potential glucocorticoid side effects. Moreover, lowering the required daily use of prednisone can also lead to the elimination of a patient's steroid induced diabetes mellitus and associated medications. As another example, the use of the combination of levocetirizine and montelukast allows patients to use decreased dosages of immunosuppressants.

In some embodiments, the combination of levocetirizine and montelukast may be used without existing therapies. In such embodiments, toxicity/side effects related to the prior use of the existing therapies, such as lenalidomide (Revlimid®) may be avoided.

Without being bound to a particularly theory, levocetirizine and montelukast work to block the H1 and leukotriene receptors, respectively. Thus, levocetirizine and montelukast effectively block the release of histamine to reduce systemic swelling/edema and improve lung function by inhibiting the release of leukotrienes. However, it is the combination of levocetirizine and montelukast, approximately 70 years newer than the prototype antihistamine, diphenhydramine that is scientifically more effective than its predecessor in reducing inflammation. Levocetirzine blocks the acute phase response to injury not only as an antihistamine but through its anti-inflammatory properties which include in part, the suppression of Interleukin 8 (IL-6) and Interleukin 8 (IL-8). IL-6 is one of the most important mediators of the acute phase reaction to injury and fever.

Moreover, levocetirizine blocks IL-8, the signaling protein responsible for chemotaxis in target cells, primarily neutrophils, causing them to migrate to the site of injury/inflammation. In addition to neutrophils there are a wide range of other cells, e.g., endothelial cells, mast cells, macrophages, and keritinocytes that respond to IL-8 as well.

Montelukast block the actions of LTD4 at the receptor. Leukotriene D4 is most potent of the cysteinyl leukotrienes in contracting airway smooth muscle. It promotes the recruitment of eosinophils, dendritic cells (antigen presenting cells) and T cells, which in turn in increases cell recruitment and activation. Clinically, montelukast has been shown to increase FEV1 by 15% in minutes to hours following administration.

Both levocetirizine and montelukast affect eosinophil quantity/migration. Eosinophil infiltration is considered by some authorities as a hallmark of inflammation. Both molecules block the acute and late phase responses to inflammation. With continuous dosing, if the acute phase is blocked, the late phase becomes less of an issue, whereas T-cell memory dissipates with time. Given the multiple sites of action within the inflammatory pathway underscored by the safety of the molecules, a unique synergy can be identified between levocetirizine and montelukast. Not limited to the treatment of immune thrombocytopenia purpura and autoimmune neutropenia, this synergy is effective in treating many forms of autoimmune disease.

As will be readily apparent to one skilled in the art, the useful in vivo dosage of levocetirizine and montelukast to be administered and the particular mode of administration will vary depending upon the age, weight, medical condition of the patient, the severity of the condition to be treated, the route of administration, the renal and hepatic function of the patient, and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Advantageously, compounds of the present embodiments may be administered, for example, in a single daily dose, or the total daily dosage may be administered in divided doses of two, three or four times daily. No complications from single daily dosing of the combination of levocetirizine and montelukast have been observed.

Definitions

The term "effective amount" includes an amount effective, at dosages and for periods of time necessary, to achieve the desired result, e.g., sufficient to treat autoimmune disorder. An effective amount of levocetirizine and montelukast may vary according to factors such as the disease state, age, and weight of the subject, and the ability of levocetirizine and montelukast to elicit a desired response in the subject. Dosage regimens may be adjusted to provide the optimum therapeutic response. An effective amount is also one in which any toxic or detrimental effects (e.g., side effects) of levocetirizine and montelukast are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between any two of these values. Such improvement or change may be observed in treated subjects as compared to subjects not treated with levocetirizine and montelukast, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s), by detection of respiratory or inflammatory disorders in a subject, and/or by modalities such as, but not limited to photographs, video, digital imaging and pulmonary function tests. Amelioration may be transient, prolonged or permanent or it may be variable at relevant times during or after levocetirizine and montelukast are administered to a subject or is used in an assay or other method described herein or a cited reference, e.g., within timeframes described infra, or about 1 hour after the administration or use of levocetirizine and montelukast to about 28 days, or 1, 3, 6, 9 months or more after a subject(s) has received such treatment.

The "modulation" of, e.g., a symptom, level or biological activity of a molecule, or the like, refers, for example, to the symptom or activity, or the like that is detectably increased or decreased. Such increase or decrease may be observed in treated subjects as compared to subjects not treated with levocetirizine and montelukast, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self assessment, by a clinician's assessment or by conducting an appropriate assay or measurement, including, e.g., quality of life assessments, suitable assays for the level or activity of molecules, cells or cell migration within a subject and/or by modalities such as, but not limited to photographs, video, digital imaging and pulmonary function tests. Modulation may be transient, prolonged or permanent or it may be variable at relevant times during or after levocetirizine and montelukast are administered to a subject or is used in an assay or other method described herein or a cited reference, e.g., within times described infra, or about 1 hour after the administration or use of levocetirizine and montelukast to about 3, 6, 9 months or more after a subject(s) has received levocetirizine and montelukast.

As used herein, the terms "prevent," "preventing," and "prevention" refer to the prevention of the recurrence, onset, or development of an autoimmune disorder. Preventing includes protecting against the occurrence and severity of upper and/or lower respiratory tract infections.

As used herein, the term "prophylactically effective amount" refers to the amount of a therapy (e.g., a pharmaceutical composition comprising montelukast and levocetirizine) which is sufficient to result in the prevention of the development, recurrence, or onset of autoimmune disorders or to enhance or improve the prophylactic effect(s) of another therapy.

As used herein, "subject" includes organisms which are capable of suffering from autoimmune disorders or other disorder treatable by a combination of montelukast and levocetirizine or who could otherwise benefit from the administration of montelukast and levocetirizine as described herein, such as human and non-human animals. Preferred human animals include human subjects. The term "non-human animals" includes all vertebrates, e.g., mammals, e.g., rodents, e.g., mice, and non-mammals, such as non-human primates, e.g., sheep, dog, cow, chickens, amphibians, reptiles, etc.

The following Examples are presented for the purposes of illustration and should not be construed as limitations.

EXAMPLES

Example 1

Case Study: Idiopathic Thrombocytopenia Purpura (ITP)

| Patient: | YS |
|---|---|
| DOB: | 1/39/1969 |
| Age: | 44 |

HPI:

Forty-four year old female originally seen and treated in our office in 2011 for recurrent epistaxis secondary to longstanding ITP (idiopathic thrombocytopenia purpura). The epistaxis was treated with the microscope and silver nitrate cautery.

The past medical history is significant for ITP diagnosed in 2000 treated with prednisone and the periodic use of IV gamma globulin. Her clinical course was complicated by streptococcal pneumonia sepsis requiring hospitalization from Jun. 30, 2004-Jul. 3, 2004. This event was underscored by the development of severe aortic insufficiency. YS thereafter underwent a splenectomy on Sep. 7, 2005 in an attempt to stabilize the low platelet count from her ITP and to prepare her for cardiac surgery. She subsequently received a mechanical aortic valve on Oct. 18, 2005. The valve itself mandates the daily administration of Coumadin® (warfarin), an anticoagulant which requires constant monitoring.

Social Hx: married, living in Santa Barbara.
Religion: Jehovah's Witness
Habits:
Alcohol—none
Tobacco—none
Coffee—one cup/day
Soda—none
Coffee—one cup/day
Tea—none
Major Medical Problems:

Idiopathic thrombocytopenia purpura-diagnosed 2000
Multiple myeloma-diagnosed 2012
Joint and skin pain secondary to the myeloma
Splenectomy-2005 with associated increase risk for infection
Cardiac surgery-aortic mechanical heart valve 2005
Recurrent epistaxis secondary to her low platelet count plus the requirement for Coumadin ®
Sepsis-2004

Surgery:

Hysterectomy without oophorectomy 2002
Laparoscopic splenectomy Sep. 7, 2005 with preoperative platelet counts of 50k-60k (normal 150k-450k)
Cardiac: mechanical aortic valve-St. Jude prosthesis, Oct. 18, 2005

Medications at the Time of the Initial Visit:

Coumadin ® (warfarin) 7-8 mg/day as an anticoagulant
Ambien CR ® (zolpidem) 12.5 mg orally at night for sleep
Ultram ® (tramadol-non-narcotic centrally acting analgesic 50 mg orally as need for pain -continued Prednisone (steroid)-intermittent use to control her platelets at a hematological safe level Pertinent Physical Examination:
Weight: 130 #58 kg/Height: 5' 9.5" 176.5 cm/BMI 18.9—normal
ENT:

| Ears | gray tympanic membranes, no hemotympanum noted |
| Nose | large 1 mm left anterior superficial vessel treated with 2% pontocaine + silver nitrate cautery |
| Throat | normal oropharynx |
| Neck | without adenopathy |

Interval Major Medical Problems: Strep pneumococcal sepsis requiring hospitalization from Feb. 20, 2012-Mar. 3, 2012
Discharge Vital Signs:
T 35.9° C./96.7° F. Pulse 67 beats/min B/P 105/75 RR 20/minute
O2 saturation on room air 100%
At the time of discharge, she was on the following medications:

Atovaquone liquid 1500 mg orally, daily, #30, for pneumocystis carinii prophylaxis
Ambien ® (zolpidem) 10 mg orally at night, #30, for insomnia
Norco ® (hydrocodone/acetaminophen) 5 mg-325 mg every four hours as needed for pain, #30
Protonix ® (pantoprazole) 40 mg orally, daily, #30, proton pump inhibitor for possible ulcer
Carafate ® (sucralfate) 1 gram/10 ml with meals and at night, #120, for possible ulcer
Coumadin (warfarin) 7-8 mg once daily anticoagulant for the mechanical aortic valve.
Lovenox ® (enoxaparin) 60 mg subcutaneously, twice a day, #20, additional anticoagulant for the mechanical heart valve
Rocephin ® (ceftriaxone) broad spectrum cephalosporin antibiotic 2 grams IV every 24 hours through Mar. 6, 2012 for strep pneumococcal sepsis
Prednisone (steroid) 60 mg orally daily #30, for ITP Clinical Course:
On Mar. 18, 2012, the patient was seen in the Santa Barbara Cottage Hospital Emergency Room for epistaxis secondary to a low platelet count of 68 k and an elevated INR of 4.67. Due to the mechanical aortic valve, the Coumadin® could not be completely discontinued without fear of a cardiac death from clotting. She was given 5 mg of Vitamin K orally, to reverse in part, the dangerously elevated INR, packed and sent home.
INR: International Normalized Ratio as an index of the propensity to form a blood clot.

| Normal range | 0.9-1.3 |
| Stroke prophylaxis for atrial fibrillation | 2.0-3.0 |
| Mechanical heart valve prophylaxis | 2.5-3.5 |

Additional Therapy: Mar. 20, 2012—Initiation of levocetirizine and montelukast
YS was thereafter seen our office on Mar. 20, 2012 with a nasal balloon in place. High dose steroids, prednisone 60 mg/day had been maintained by her Hematologist/Oncologist to stabilize the bone marrow and underlying disease process post sepsis and hospitalization.

Laboratory Data:

| Mar. 18, 2012 | Mar. 20, 2012 |
|---|---|
| WBC-4.9k/μL | WBC-4.9k/μL |
| Hgb-9.2 gm/dL | Hgb-9.6 gm/dL |
| Hct-27.8% | Hct-29.1% |
| Platelet count-68k/μL | Platelet count-53k/μL |

Initiated to complement to the ITP treatment protocol were levocetirizine 5 mg orally daily+montelukast 10 mg orally daily as dual, safe, steroid sparing, anti-inflammatory agents. Ferrous gluconate (iron) 324 mg plus Vitamin C 500 mg to aid absorption of the iron was also suggested to restore the hemoglobin and hematocrit to normal levels.

Significantly improved platelet values were sustained above 100 k/μL from a baseline of 50 k-60 k/μL (normal 150 k—45014.0 from mid-April 2012 through early September 2012 as shown in FIG. 2A-2C. FIG. 2A shows the platelet counts 6 days after the initiation of treatment with levocetirizine and montelukast. From a platelet count of 53 k, the level rose to a 10 year high of 183 k.μL, only six days after treatment was initiated. To reiterate, baseline platelet counts were traditionally between 50 k-60 k/μL. The numbers in early March 2012 reflect the response to high dose prednisone 60 mg/day started during the hospitalization for sepsis (Feb. 20, 2012-Mar. 3, 2012). Prednisone was tapered to 15 mg/day in June 2012.

Overview:
This case is a clinical example of the remarkable anti-inflammatory synergy between two extremely safe, Pregnancy Category B molecules: levocetirizine plus montelukast for the treatment of ITP (idiopathic thrombocytopenia purpura).

As previously mentioned, the combination of levocetirizine and montelukast is steroid sparing. The molecules can be used to: (a) augment existing therapies or (b) primarily in certain cases without resorting to the use of steroids or other immune modulating agents, many of which are extremely toxic (e.g., lenalidomide (Revlimid®). Lower doses of steroids decrease the risk of developing opportunistic infection, electrolyte imbalance, weight gain, fluid retention, cataract formation, hypertension, diabetes mellitus, and osteoporosis to iterate just a few of the myriad of potential steroid side effects.

There have been no complications from the single daily dosing of levocetirizine plus montelukast.

Example 2

Case Study: 69-year-old female with Autoimmune Neutropenia and Steroid Induced Diabetes Mellitus

| Patient | PB |
|---|---|
| DOB | Feb. 13, 1944 |
| Age | 69 |

The patient is a 69-year-old female seen and evaluated in the office in 2011 for the evaluation of sphenoid sinusitis present on imaging in 2008. The rhinosinusitis was underscored a history of chronic autoimmune neutropenia diagnosed via bone marrow biopsy in December 1997. The onset of neutropenia was preceded by pesticide exposure a few months earlier.

The past medical history is complicated by deep venous thrombosis requiring Coumadin® prophylaxis, severe rheumatoid arthritis, hypertension and steroid induced diabetes mellitus. Without prednisone she experiences significant joint pain and swelling of the hands.

Occupational History: retired Computer Scientist
Major Medical Problems:
Autoimmune neutropenia
Severe rheumatoid arthritis
History of deep venous thrombosis and pulmonary embolism September 2010 due to a lupus anticoagulant
Stroke Mar. 3, 2011 affecting the right leg
Chronic sphenoid sinusitis
Diabetes mellitus (steroid induced)
Severe vasculitis
Splenomegaly
Hypothyroidism on replacement
Chronic prednisone use
Steroid induced hypertension, adrenal suppression, diabetes mellitus, weight gain, fluid retention, and osteopenia
Pulmonary artery hypertension
Right costophrenic angle cavity mass—3.4 cm consistent with a lung infarct
Medications on Presentation Jan. 17, 2011:

Medrol (steroid) 24 mg daily for autoimmune neutropenia
Methotrexate (immunosuppressant)15 mg/week for arthritis
Humalog ® sliding scale insulin averaging 8 units subcutaneously in the AM and 10 units at dinner (injectable short acting insulin to control elevated blood sugar)
Metformin 500 mg three time per day (decreases hepatic glucose production and intestinal glucose absorption; increases insulin sensitivity)
Glimepiride 4 mg per day (sulfonylurea which stimulates pancreatic islet beta cell insulin release)
Armour ® thyroid 120 mg daily (thyroid hormone replacement)
Plaquenil ® (hydroxychloroquine) 400 mg per day/anti-malarial drug used off-label for immune disorders
Spironolactone 50 mg twice a day (potassium sparing diuretic used to control steroid induced
Coumadin ® (warfarin) 3.5 mg daily for DVT (deep venous thrombosis) prophylaxis Supplements:

DHEA 25 mg orally twice a day to mitigate adrenal suppression caused by the chronic use of steroids
Iodine/Iodide 12.5 mg per day
Vitamin D3 2000 units/day
Potassium 8 meg/day to supplement potassium loss from use of the diuretic
Calcium one capsule in the AM to help control osteoporosis caused by the steroids
Iron capsule one daily
Vitamin C 1000 mg daily
Folic acid one tablet per day to counteract folate depletion and resultant anemia caused by the methotrexate As Needed:
Lovenox® (enoxaparin) 200 mg injected as needed to augment the anti-coagulant effect of the Coumadin®
Neupogen® (filgrastim) to increase the white blood cell count when the absolute neutrophil count is below one thousand. Neupogen® stimulates granulocyte and macrophage proliferation and differentiation.
Allergies/Sensitivity to Medication:

Penicillin-urticaria as a teenager
Avelox ® (moxifloxacin)-central nervous system stimulation
Sulfa-nausea
Codeine-nausea
Metformin-nausea Surgery:

Parathyroidectomy-1998
Cholecystectomy-1999
Placement of a venous umbrella filter (IVC-inferior vena cava) 2010

Habits:

Tobacco use-none
Alcohol-none
Tea-5 cups of herbal tea/week
Coffee-2 cups/month-decaffeinated
Soda-2 per month Pertinent Physical Examination:
Vital signs: T 96.5° F. 35.8° C. B/P 151/81 Pulse 84 beats/minute Respiratory rate 14/minute
Weight: 204-218 #/92.7-99 kg Height: 5'8"/172.7 cm BMI 31.0/Obesity Class I/III

ENT:

| Ears | 10x micro/gray tympanic membranes, mild tympanosclerosis, no middle ear effusion |
| --- | --- |
| Nose | anterior erythema consistent with a *Staphylococcus aureus* carrier state |
| Throat | 0.5+/4+ tonsils, normal oropharynx |
| Larynx | mild erythema, clear secretions |
| Neck | without adenopathy |

Laboratory Data:
Aug. 26, 2010

WBC (white blood cell count): 0.5k/μL low (normal range 4.5-10.5k/μL)
Absolute white blood cell count: 140/μL -continued

| Assessment from outside records: | prolonged neutropenia, currently on levofloxacin (quinolone antibiotic) and nystatin (antifungal). Neupogen ® (filgrastim) initiated to increase the white blood cell count. |
|---|---|

Dec. 31, 2010

| | |
|---|---|
| WBC (white blood cell count): | 2.7k/µL low (normal range 4.5-10.5k/µL) |
| WBC (white blood cell count): | 2.8k/µL low (normal range 4.5-10.5k/µL) |
| Absolute white blood cell count: | 1.89k/µL on 35 mg of prednisone |
| Hg (hemoglobin): | 11.6 gm/dL low (normal 12.0-16.0) |
| Hct (hematocrit): | 35.9% low ( 36.0-46.0) |
| Platelet count: | 230,000/µL |
| Kidney function: Creatinine | 0.7 mg/dl (normal 0.5-1.6 mg/dl) |
| Liver enzymes: | |
| ALT (SGPT) | 48 IU/L elevated (normal 2-45) |
| AST (SGOT) | 24 IU/L (normal 2-50) |
| Index of inflammation/infection: | |
| CRP (C-reactive protein) | 7.88 mg/L elevated (normal 0.07-4.94) |
| Sed Rate (sedimentation rate) | 9 mm/hour (normal 0-20) |

Jun. 27, 2011

Assessment: 69 year old female with autoimmune neutropenia (diagnosed in 1997), severe rheumatoid arthritis and steroid induced diabetes mellitus Clinical Course/Treatment Regimen: Jun. 28, 2011: Initiated levocetirizine and montelukast The patient was seen in follow-up on Jun. 28, 2011 to review records regarding her chronic sinusitis. In the interim she had experienced a stroke on Mar. 3, 2011 affecting her left lower extremity. The Coumadin® (warfarin) was subsequently replaced by Lovenox® (enoxaparin) 130 mg injected subcutaneously every 24 hours plus Plavix® (clopidogrel) 75 mg orally per day. The Medrol® (methylprednisolone) 24 mg had been replaced by prednisone 35 mg per day and methotrexate increased to 90 mg once a week.

Due to the high-risk nature of potential sphenoid sinus surgery, a medical option consisting of a six month trial of levocetirizine+montelukast was discussed. The products, safety, pathway and science were reviewed in detail. She was subsequently begun on levocetirizine 5 mg daily plus montelukast 10 mg daily on Jun. 28, 2011.

On Aug. 24, 2011, PB was independently seen by her oncologist at the Sansum Santa Barbara Medical Foundation Clinic. A quote from that medical record is as follows: "What appears to be miraculous is that this patient since starting Dr. May's levocetirizine and montelukast her white count has normalized. In July 2011, her white count was 2.8K with 73% neutrophils. In August 2011 her white count was 4.6 k/4 with 90% neutrophils. Her CRP (C-reactive protein, an index for inflammation, normal <10) is down to 7.5. Her Sedimentation Rate (another index of inflammation, normal 0-20) is 6. Clinically she is "feeling fine."

Effect of Sustained Treatment with Levocetirizine Plus Montelukast

The patient has been maintained on levocetirizine plus montelukast since Jun. 28, 2011. Her white blood cell count has stabilized to the highest averaged levels in 10 years. Her total white blood cell count has not been below 2.6 k/µL at any time in the past nineteen months. Recent counts were 5.5 K/µL, Nov. 5, 2012, 4.5 K/µL, Dec. 4, 2012 and 4.1 K/µL, Jan. 22, 2013. Both prednisone and methotrexate were tapered to 20 mg/day and 20 mg/week, respectively on Aug. 23, 2011, approximately two months following the initiation of the new treatment protocol. On Dec. 15, 2011 the prednisone was reduced to 15 mg/day, thereby eliminating her diabetes mellitus and associated medications.

Overview:

This case is a clinical example of the remarkable anti-inflammatory synergy between two extremely safe molecules: levocetirizine plus montelukast for the treatment of one form of autoimmune disease, autoimmune neutropenia. The combination therapy has stabilized the patient's white blood cell count and dramatically improved quality of life by lowering the required daily use of prednisone. This reduction has led to the elimination of her steroid induced diabetes mellitus.

What is claimed is:

1. A method of treating an autoimmune disorder or a symptom of autoimmune disorder caused by an autoimmune disorder in a patient in need thereof comprising administering to the patient an effective amount of a combination of levocetirizine and montelukast; wherein the autoimmune disorder is rheumatoid arthritis.

2. The method of claim 1, wherein the combination is administered at the onset of symptoms.

3. The method of claim 1, wherein the combination is administered in a sequential manner.

4. The method of claim 1, wherein the combination is administered in a substantially simultaneous manner.

5. The method of claim 1, further comprising the administration of an additional active agent.

6. The method of claim 5, wherein the additional active agent is a steroid.

7. The method of claim 5, wherein the additional active agent is a glucocorticoid.

8. The method of claim 7, wherein the glucocorticoid is prednisone or methyl-prednisolone.

9. The method of claim 5, wherein the additional active agent is an immunosuppressant.

10. The method of claim 9, wherein the immunosuppressant is methotrexate.

11. The method of claim 5, wherein the additional active agent is a supplement.

12. The method of claim 11, wherein the supplement is ferrous gluconate or vitamin C.

13. The method of claim 5, wherein the additional active agent is an antibacterial.

14. The method of claim 13, wherein the additional active agent is dapsone.

15. The method of claim 5, wherein the additional active agent is a protein.

16. The method of claim 15, wherein the protein is filgrastim.

17. The method of claim 5, wherein the additional active agent is an immunomodulator.

18. The method of claim 17, wherein the immunomodulator is lenalidomide.

19. The method of claim 1, wherein the combination is administered to the patient by one or more of the routes consisting of enteral, intravenous, intraperitoneal, inhalation, intramuscular, subcutaneous and oral.

20. The method of claim 1, wherein the levocetirizine and montelukast are administered by the same route.

21. A method of treating an autoimmune disorder or a symptom of autoimmune disorder caused by an autoimmune disorder in a patient in need thereof comprising administering to the patient an effective amount of a combination of levocetirizine, montelukast, and an additional active agent selected from filgrastim and lenalidomide.

22. A method of treating an autoimmune disorder or a symptom of autoimmune disorder caused by an autoimmune disorder in a patient in need thereof comprising administering to the patient an effective amount of a combination of levocetirizine and montelukast; wherein the autoimmune disorder is rheumatoid arthritis; and wherein the combination of levocetirizine and montelukast is configured to normalize white blood cell count in the patient.

* * * * *